United States Patent
Patel et al.

(10) Patent No.: US 9,510,542 B2
(45) Date of Patent: Dec. 6, 2016

(54) CANOLA VARIETY 45H76

(71) Applicant: PIONEER HI-BRED INTERNATIONAL INC, Johnston, IA (US)

(72) Inventors: Jayantilal Devabhai Patel, Thornhill (CA); Julian Heath, Saskatoon (CA)

(73) Assignee: PIONEER HI-BRED INTERNATIONAL, INC., Johnston, IA (US)

( * ) Notice: Subject to any disclaimer, the term of this patent is extended or adjusted under 35 U.S.C. 154(b) by 90 days.

(21) Appl. No.: 14/633,185

(22) Filed: Feb. 27, 2015

(65) Prior Publication Data

US 2016/0249565 A1   Sep. 1, 2016

(51) Int. Cl.
| | |
|---|---|
| *A01H 5/10* | (2006.01) |
| *A01H 1/02* | (2006.01) |
| *C12N 15/82* | (2006.01) |
| *A01H 1/08* | (2006.01) |

(52) U.S. Cl.
CPC ........ *A01H 5/10* (2013.01); *A01H 1/02* (2013.01); *A01H 1/08* (2013.01); *C12N 15/8243* (2013.01); *C12N 15/8245* (2013.01); *C12N 15/8247* (2013.01); *C12N 15/8251* (2013.01); *C12N 15/8271* (2013.01); *C12N 15/8274* (2013.01); *C12N 15/8279* (2013.01); *C12N 15/8286* (2013.01); *C12N 15/8289* (2013.01)

(58) Field of Classification Search
None
See application file for complete search history.

(56) References Cited

U.S. PATENT DOCUMENTS

| | | | |
|---|---|---|---|
| 8,865,975 B1 | 10/2014 | Patel | |
| 8,895,809 B1 * | 11/2014 | Patel | ........................ A01H 5/10 435/430 |

* cited by examiner

*Primary Examiner* — Elizabeth McElwain
(74) *Attorney, Agent, or Firm* — Pioneeer Hi-Bred Int'l, Inc.

(57) ABSTRACT

Provided is a canola variety designated 45H76 and seed, plants and plant parts thereof produced from a cross of inbred varieties. Methods for producing a canola variety comprise crossing canola variety 45H76 with another canola plant. Methods for producing a canola plant containing in its genetic material one or more traits introgressed into 45H76 through backcross conversion and/or transformation, and to the canola seed, plant and plant part produced thereby are described. Canola variety 45H76, the seed, the plant produced from the seed, plant parts and variants, mutants, and minor modifications of canola variety 45H76 are disclosed.

20 Claims, No Drawings

CANOLA VARIETY 45H76

FIELD

The discovery is in the field of *Brassica napus* breeding (i.e., canola breeding), specifically relating to the canola variety designated 45H76.

BACKGROUND

The present discovery relates to a novel rapeseed variety designated 45H76 which is the result of years of careful breeding and selection. Since such variety is of high quality and possesses a relatively low level of erucic acid in the vegetable oil component and a relatively low level of glucosinolate content in the meal component, it can be termed "canola" in accordance with the terminology commonly used by plant scientists.

The goal of plant breeding is to combine in a single variety or hybrid various desirable traits. For field crops, these traits may include resistance to diseases and insects, tolerance to heat and drought, reducing the time to crop maturity, greater yield, and better agronomic quality. With mechanical harvesting of many crops, uniformity of plant characteristics such as germination and stand establishment, growth rate, maturity, and plant and pod height, is important. The creation of new superior, agronomically sound, and stable high-yielding cultivars of many plant types including canola has posed an ongoing challenge to plant breeders. Therefore, there is a continuing need in the field of agriculture for canola plants having desirable agronomic and industrial characteristics.

SUMMARY

A novel *Brassica napus* variety designated 45H76 is provided. This discovery thus relates to the seeds of the 45H76 variety, to plants of the 45H76 variety, and to methods for producing a canola plant by crossing the 45H76 variety with itself or another canola plant (whether by use of male sterility or open pollination), and to methods for producing a canola plant containing in its genetic material one or more transgenes, and to transgenic plants produced by that method. This discovery also relates to canola seeds and plants produced by crossing the variety 45H76 with another line.

DEFINITIONS

In the description and tables which follow, a number of terms are used. In order to aid in a clear and consistent understanding of the specification, the following definitions and evaluation criteria are provided.

Anther Fertility. The ability of a plant to produce pollen; measured by pollen production. 1=sterile, 9=all anthers shedding pollen (vs. Pollen Formation which is amount of pollen produced).

Anther Arrangement. The general disposition of the anthers in typical fully opened flowers is observed.

Chlorophyll Content. The typical chlorophyll content of the mature seeds is determined by using methods recommended by the Western Canada Canola/Rapeseed Recommending Committee (WCC/RRC). 1=low (less than 8 ppm), 2=medium (8 to 15 ppm), 3=high (greater than 15 ppm). Also, chlorophyll could be analyzed using NIR (Near Infrared) spectroscopy as long as the instrument is calibrated according to the manufacturer's specifications.

CMS. Abbreviation for cytoplasmic male sterility.

Cotyledon. A cotyledon is a part of the embryo within the seed of a plant; it is also referred to as a seed leaf. Upon germination, the cotyledon may become the embryonic first leaf of a seedling.

Cotyledon Length. The distance between the indentation at the top of the cotyledon and the point where the width of the petiole is approximately 4 mm.

Cotyledon Width. The width at the widest point of the cotyledon when the plant is at the two to three-leaf stage of development. 3=narrow, 5=medium, 7=wide.

CV %: Abbreviation for coefficient of variation.

Disease Resistance: Resistance to various diseases is evaluated and is expressed on a scale of 0=not tested, 1=resistant, 3=moderately resistant, 5=moderately susceptible, 7=susceptible, and 9=highly susceptible.

Erucic Acid Content: The percentage of the fatty acids in the form of C22:1.as determined by one of the methods recommended by the WCC/RRC, being AOCS Official Method Ce 2-66 Preparation of Methyl esters of Long-Chain Fatty Acids or AOCS Official Method Ce 1-66 Fatty Acid Composition by Gas Chromatography.

Fatty Acid Content: The typical percentages by weight of fatty acids present in the endogenously formed oil of the mature whole dried seeds are determined. During such determination the seeds are crushed and are extracted as fatty acid methyl esters following reaction with methanol and sodium methoxide. Next the resulting ester is analyzed for fatty acid content by gas liquid chromatography using a capillary column which allows separation on the basis of the degree of unsaturation and fatty acid chain length. This procedure is described in the work of Daun, et al., (1983) *J. Amer. Oil Chem. Soc.* 60:1751 to 1754 which is herein incorporated by reference.

Flower Bud Location. A determination is made whether typical buds are disposed above or below the most recently opened flowers.

Flower Date 50%. (Same as Time to Flowering) The number of days from planting until 50% of the plants in a planted area have at least one open flower.

Flower Petal Coloration. The coloration of open exposed petals on the first day of flowering is observed.

Frost Tolerance (Spring Type Only). The ability of young plants to withstand late spring frosts at a typical growing area is evaluated and is expressed on a scale of 1 (poor) to 5 (excellent).

Gene Silencing. The interruption or suppression of the expression of a gene at the level of transcription or translation.

Genotype. Refers to the genetic constitution of a cell or organism.

Glucosinolate Content. The total glucosinolates of seed at 8.5% moisture, as measured by AOCS Official Method AK-1-92 (determination of glucosinolates content in rapeseed—colza by HPLC), is expressed as micromoles per gram of defatted, oil-free meal. Capillary gas chromatography of the trimethylsityl derivatives of extracted and purified desulfoglucosinolates with optimization to obtain optimum indole glucosinolate detection is described in "*Procedures of the Western Canada Canola/Rapeseed Recommending Committee Incorporated for the Evaluation and Recommendation for Registration of Canola/Rapeseed Candidate Cultivars in Western Canada*". Also, glucosinolates could be analyzed using NIR (Near Infrared) spectroscopy as long as the instrument is calibrated according to the manufacturer's specifications.

Grain. Seed produced by the plant or a self or sib of the plant that is intended for food or feed use.

Green Seed. The number of seeds that are distinctly green throughout as defined by the Canadian Grain Commission. Expressed as a percentage of seeds tested.

Herbicide Resistance: Resistance to various herbicides when applied at standard recommended application rates is expressed on a scale of 1 (resistant), 2 (tolerant), or 3 (susceptible).

Leaf Anthocyanin Coloration. The presence or absence of leaf anthocyanin coloration, and the degree thereof if present, are observed when the plant has reached the 9- to 11-leaf stage.

Leaf Attachment to Stem. The presence or absence of clasping where the leaf attaches to the stem, and when present the degree thereof, are observed.

Leaf Attitude. The disposition of typical leaves with respect to the petiole is observed when at least 6 leaves of the plant are formed.

Leaf Color. The leaf blade coloration is observed when at least six leaves of the plant are completely developed.

Leaf Glaucosity. The presence or absence of a fine whitish powdery coating on the surface of the leaves, and the degree thereof when present, are observed.

Leaf Length. The length of the leaf blades and petioles are observed when at least six leaves of the plant are completely developed.

Leaf Lobes. The fully developed upper stem leaves are observed for the presence or absence of leaf lobes when at least 6 leaves of the plant are completely developed.

Leaf Margin Indentation. A rating of the depth of the indentations along the upper third of the margin of the largest leaf. 1=absent or very weak (very shallow), 3=weak (shallow), 5=medium, 7=strong (deep), 9=very strong (very deep).

Leaf Margin Hairiness. The leaf margins of the first leaf are observed for the presence or absence of pubescence, and the degree thereof, when the plant is at the two leaf-stage.

Leaf Margin Shape. A visual rating of the indentations along the upper third of the margin of the largest leaf. 1=undulating, 2=rounded, 3=sharp.

Leaf Surface. The leaf surface is observed for the presence or absence of wrinkles when at least six leaves of the plant are completely developed.

Leaf Tip Reflexion. The presence or absence of bending of typical leaf tips and the degree thereof, if present, are observed at the six to eleven leaf-stage.

Leaf Upper Side Hairiness. The upper surfaces of the leaves are observed for the presence or absence of hairiness, and the degree thereof if present, when at least six leaves of the plant are formed.

Leaf Width. The width of the leaf blades is observed when at least six leaves of the plant are completely developed.

Locus. A specific location on a chromosome.

Locus Conversion. A locus conversion refers to plants within a variety that have been modified in a manner that retains the overall genetics of the variety and further comprises one or more loci with a specific desired trait, such as male sterility, insect, disease or herbicide resistance. Examples of single locus conversions include mutant genes, transgenes and native traits finely mapped to a single locus. One or more locus conversion traits may be introduced into a single canola variety.

Lodging Resistance. Resistance to lodging at maturity is observed. 1=not tested, 3=poor, 5=fair, 7=good, 9=excellent.

LSD. Abbreviation for least significant difference.

Maturity. The number of days from planting to maturity is observed, with maturity being defined as the plant stage when pods with seed change color, occurring from green to brown or black, on the bottom third of the pod-bearing area of the main stem.

NMS. Abbreviation for nuclear male sterility.

Number of Leaf Lobes. The frequency of leaf lobes, when present, is observed when at least six leaves of the plant are completely developed.

Oil Content: The typical percentage by weight oil present in the mature whole dried seeds is determined by ISO 10565:1993 Oilseeds Simultaneous determination of oil and water—Pulsed NMR method. Also, oil could be analyzed using NIR (Near Infrared) spectroscopy as long as the instrument is calibrated according to the manufacturer's specifications, reference AOCS Procedure Am 1-92 Determination of Oil, Moisture and Volatile Matter, and Protein by Near-Infrared Reflectance.

Pedicel Length. The typical length of the silique stem when mature is observed. 3=short, 5=medium, 7=long.

Petal Length. The lengths of typical petals of fully opened flowers are observed. 3=short, 5=medium, 7=long.

Petal Width. The widths of typical petals of fully opened flowers are observed. 3=short, 5=medium, 7=long.

Petiole Length. The length of the petioles is observed, in a line forming lobed leaves, when at least six leaves of the plant are completely developed. 3=short, 5=medium, 7=long.

Plant Height. The overall plant height at the end of flowering is observed. 3=short, 5=medium, 7=tall.

Ploidy. This refers to the number of chromosomes exhibited by the line, for example diploid or tetraploid.

Pod Anthocyanin Coloration. The presence or absence at maturity of silique anthocyanin coloration, and the degree thereof if present, are observed.

Pod (Silique) Beak Length. The typical length of the silique beak when mature is observed. 3=short, 5=medium, 7=long.

Pod Habit. The typical manner in which the siliques are borne on the plant at maturity is observed.

Pod (Silique) Length. The typical silique length is observed. 1=short (less than 7 cm), 5=medium (7 to 10 cm), 9=long (greater than 10 cm).

Pod (Silique) Attitude. A visual rating of the angle joining the pedicel to the pod at maturity. 1=erect, 3=semi-erect, 5=horizontal, 7=semi-drooping, 9=drooping.

Pod Type. The overall configuration of the silique is observed.

Pod (Silique) Width. The typical pod width when mature is observed. 3=narrow (3 mm), 5=medium (4 mm), 7=wide (5 mm).

Pollen Formation. The relative level of pollen formation is observed at the time of dehiscence.

Protein Content: The typical percentage by weight of protein in the oil free meal of the mature whole dried seeds is determined by AOCS Official Method Ba 4e-93 Combustion Method for the Determination of Crude Protein. Also, protein could be analyzed using NIR (Near Infrared) spectroscopy as long as the instrument is calibrated according to the manufacturer's specifications, reference AOCS Procedure Am 1-92 Determination of Oil, Moisture and Volatile Matter, and Protein by Near-Infrared Reflectance.

Resistance. The ability of a plant to withstand exposure to an insect, disease, herbicide, or other condition. A resistant plant variety or hybrid will have a level of resistance higher than a comparable wild-type variety or hybrid. "Tolerance" is a term commonly used in crops such as canola, soybean, and sunflower affected by an insect, disease, such as *Sclerotinia*, herbicide, or other condition and is used to describe an improved level of field resistance.

Root Anthocyanin Coloration. The presence or absence of anthocyanin coloration in the skin at the top of the root is observed when the plant has reached at least the six-leaf stage.

Root Anthocyanin Expression. When anthocyanin coloration is present in skin at the top of the root, it further is observed for the exhibition of a reddish or bluish cast within such coloration when the plant has reached at least the six-leaf stage.

Root Anthocyanin Streaking. When anthocyanin coloration is present in the skin at the top of the root, it further is observed for the presence or absence of streaking within such coloration when the plant has reached at least the six-leaf stage.

Root Chlorophyll Coloration. The presence or absence of chlorophyll coloration in the skin at the top of the root is observed when the plant has reached at least the six-leaf stage.

Root Coloration Below Ground. The coloration of the root skin below ground is observed when the plant has reached at least the six-leaf stage.

Root Depth in Soil. The typical root depth is observed when the plant has reached at least the six-leaf stage.

Root Flesh Coloration. The internal coloration of the root flesh is observed when the plant has reached at least the six-leaf stage.

SE. Abbreviation for standard error.

Seedling Growth Habit. The growth habit of young seedlings is observed for the presence of a weak or strong rosette character. 1=weak rosette, 9=strong rosette.

Seeds Per Pod. The average number of seeds per pod is observed.

Seed Coat Color. The seed coat color of typical mature seeds is observed. 1=black, 2=brown, 3=tan, 4=yellow, 5=mixed, 6=other.

Seed Coat Mucilage. The presence or absence of mucilage on the seed coat is determined and is expressed on a scale of 1 (absent) to 9 (present). During such determination a petri dish is filled to a depth of 0.3 cm. with water provided at room temperature. Seeds are added to the petri dish and are immersed in water where they are allowed to stand for five minutes. The contents of the petri dish containing the immersed seeds are then examined under a stereo microscope equipped with transmitted light. The presence of mucilage and the level thereof is observed as the intensity of a halo surrounding each seed.

Seed Size. The weight in grams of 1,000 typical seeds is determined at maturity while such seeds exhibit a moisture content of approximately 5 to 6 percent by weight.

Shatter Resistance. Resistance to silique shattering is observed at seed maturity. 1=not tested, 3=poor, 5=fair, 7=good, 9=does not shatter.

SI. Abbreviation for self-incompatible.

Speed of Root Formation. The typical speed of root formation is observed when the plant has reached the four to eleven-leaf stage.

SSFS. Abbreviation for *Sclerotinia sclerotiorum* Field Severity score, a rating based on both percentage infection and disease severity.

Stem Anthocyanin Intensity. The presence or absence of leaf anthocyanin coloration and the intensity thereof, if present, are observed when the plant has reached the nine to eleven-leaf stage. 1=absent or very weak, 3=weak, 5=medium, 7=strong, 9=very strong.

Stem Lodging at Maturity. A visual rating of a plant's ability to resist stem lodging at maturity. 1=very weak (lodged), 9=very strong (erect).

Time to Flowering. A determination is made of the number of days when at least 50 percent of the plants have one or more open buds on a terminal raceme in the year of sowing.

Seasonal Type. This refers to whether the new line is considered to be primarily a Spring or Winter type of canola.

Winter Survival (Winter Type Only). The ability to withstand winter temperatures at a typical growing area is evaluated and is expressed on a scale of 1 (poor) to 5 (excellent).

DETAILED DESCRIPTION

Field crops are bred through techniques that take advantage of the plant's method of pollination. A plant is self-pollinated if pollen from one flower is transferred to the same or another flower of the same plant or a genetically identical plant. A plant is sib-pollinated when individuals within the same family or line are used for pollination. A plant is cross-pollinated if the pollen comes from a flower on a genetically different plant from a different family or line. The term "cross-pollination" used herein does not include self-pollination or sib-pollination.

In the practical application of a chosen breeding program, the breeder often initially selects and crosses two or more parental lines, followed by repeated selfing and selection, thereby producing many unique genetic combinations. The breeder can theoretically generate billions of different genetic combinations via crossing, selfing and mutagenesis. However, the breeder commonly has no direct control at the cellular level of the plant. Therefore, two breeders will never independently develop the same variety having the same canola traits.

In each cycle of evaluation, the plant breeder selects the germplasm to advance to the next generation. This germplasm is grown under chosen geographical, climatic and soil conditions, and further selections are then made during and at the end of the growing season. The characteristics of the varieties developed are incapable of prediction in advance. This unpredictability is because the selection occurs in unique environments, with no control at the DNA level (using conventional breeding procedures), and with millions of different possible genetic combinations being generated. A breeder of ordinary skill cannot predict in advance the final resulting varieties that are to be developed, except possibly in a very gross and general fashion. Even the same breeder is incapable of producing the same variety twice by using the same original parents and the same selection techniques. This unpredictability commonly results in the expenditure of large research monies and effort to develop a new and superior canola variety.

Canola breeding programs utilize techniques such as mass and recurrent selection, backcrossing, pedigree breeding and haploidy. For a general description of rapeseed and Canola breeding, see, Downey and Rakow, (1987) "Rapeseed and Mustard" In: *Principles of Cultivar Development*, Fehr, (ed.), pp 437-486; New York; Macmillan and Co.; Thompson, (1983) "Breeding winter oilseed rape *Brassica napus*"; *Advances in Applied Biology* 7:1-104; and Ward, et. al., (1985) Oilseed Rape, Farming Press Ltd., Wharfedale Road, Ipswich, Suffolk, each of which is hereby incorporated by reference.

Recurrent selection is used to improve populations of either self- or cross-pollinating *Brassica*. Through recurrent selection, a genetically variable population of heterozygous individuals is created by intercrossing several different parents. The best plants are selected based on individual superiority, outstanding progeny, and/or excellent combining ability. The selected plants are intercrossed to produce a new population in which further cycles of selection are continued. Various recurrent selection techniques are used to improve quantitatively inherited traits controlled by numerous genes.

Breeding programs use backcross breeding to transfer genes for a simply inherited, highly heritable trait into another line that serves as the recurrent parent. The source of the trait to be transferred is called the donor parent. After the initial cross, individual plants possessing the desired trait of the donor parent are selected and are crossed (backcrossed) to the recurrent parent for several generations. The resulting plant is expected to have the attributes of the recurrent parent and the desirable trait transferred from the donor parent. This approach has been used for breeding disease resistant phenotypes of many plant species, and has been used to transfer low erucic acid and low glucosinolate content into lines and breeding populations of *Brassica*.

Pedigree breeding and recurrent selection breeding methods are used to develop varieties from breeding populations. Pedigree breeding starts with the crossing of two genotypes, each of which may have one or more desirable characteristics that is lacking in the other or which complements the other. If the two original parents do not provide all of the desired characteristics, other sources can be included in the breeding population. In the pedigree method, superior plants are selfed and selected in successive generations. In the succeeding generations the heterozygous condition gives way to homogeneous lines as a result of self-pollination and selection. Typically in the pedigree method of breeding, five or more generations of selfing and selection are practiced: $F_1$ to $F_2$; $F_2$ to $F_3$; $F_3$ to $F_4$; $F_4$ to $F_5$, etc. For example, two parents that are believed to possess favorable complementary traits are crossed to produce an $F_1$. An $F_2$ population is produced by selfing one or several $F_1$'s or by intercrossing two $F_1$'s (i.e., sib mating). Selection of the best individuals may begin in the $F_2$ population, and beginning in the $F_3$ the best individuals in the best families are selected. Replicated testing of families can begin in the $F_4$ generation to improve the effectiveness of selection for traits with low heritability. At an advanced stage of inbreeding (i.e., $F_6$ and $F_7$), the best lines or mixtures of phenotypically similar lines commonly are tested for potential release as new cultivars. Backcrossing may be used in conjunction with pedigree breeding; for example, a combination of backcrossing and pedigree breeding with recurrent selection has been used to incorporate blackleg resistance into certain cultivars of *Brassica napus*.

Plants that have been self-pollinated and selected for type for many generations become homozygous at almost all gene loci and produce a uniform population of true breeding progeny. If desired, double-haploid methods can also be used to extract homogeneous lines. A cross between two different homozygous lines produces a uniform population of hybrid plants that may be heterozygous for many gene loci. A cross of two plants each heterozygous at a number of gene loci will produce a population of hybrid plants that differ genetically and will not be uniform.

The choice of breeding or selection methods depends on the mode of plant reproduction, the heritability of the trait(s) being improved, and the type of cultivar used commercially, such as $F_1$ hybrid variety or open pollinated variety. A true breeding homozygous line can also be used as a parental line (inbred line) in a commercial hybrid. If the line is being developed as an inbred for use in a hybrid, an appropriate pollination control system should be incorporated in the line. Suitability of an inbred line in a hybrid combination will depend upon the combining ability (general combining ability or specific combining ability) of the inbred.

Various breeding procedures are also utilized with these breeding and selection methods. The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

In a multiple-seed procedure, canola breeders commonly harvest one or more pods from each plant in a population and thresh them together to form a bulk. Part of the bulk is used to plant the next generation and part is put in reserve. The procedure has been referred to as modified single-seed descent or the pod-bulk technique. The multiple-seed procedure has been used to save labor at harvest. It is considerably faster to thresh pods with a machine than to remove one seed from each by hand for the single-seed procedure. The multiple-seed procedure also makes it possible to plant the same number of seeds of a population each generation of inbreeding. Enough seeds are harvested to make up for those plants that did not germinate or produce seed. If desired, doubled-haploid methods can be used to extract homogeneous lines.

Molecular markers, including techniques such as Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) and Single Nucleotide Polymorphisms (SNPs), may be used in plant breeding methods. One use of molecular markers is Quantitative Trait Loci (QTL) mapping. QTL mapping is the use of markers which are known to be closely linked to alleles that have measurable effects on a quantitative trait. Selection in the breeding process is based upon the accumulation of markers linked to the positive effecting alleles and/or the elimination of the markers linked to the negative effecting alleles in the plant's genome.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select for the genome of the recurrent parent and against the markers of the donor parent. Using this procedure can minimize the amount of genome from the donor parent that remains in the selected plants. It can also be used to reduce the number of crosses back to the recurrent parent needed in a backcrossing program. The use of molecular markers in the selection process is often called Genetic Marker Enhanced Selection or Marker Assisted Selection (MAS).

The production of doubled haploids can also be used for the development of inbreds in the breeding program. In

*Brassica napus*, microspore culture technique is used in producing haploid embryos. The haploid embryos are then regenerated on appropriate media as haploid plantlets, doubling chromosomes of which results in doubled haploid plants. This can be advantageous because the process omits the generations of selfing needed to obtain a homozygous plant from a heterozygous source.

The development of a canola hybrid in a canola plant breeding program involves three steps: (1) the selection of plants from various germplasm pools for initial breeding crosses; (2) the selfing of the selected plants from the breeding crosses for several generations to produce a series of inbred lines, which, although different from each other, breed true and are highly uniform; and (3) crossing the selected inbred lines with different inbred lines to produce the hybrids. During the inbreeding process in canola, the vigor of the lines decreases. Vigor is restored when two different inbred lines are crossed to produce the hybrid. An important consequence of the homozygosity and homogeneity of the inbred lines is that the hybrid between a defined pair of inbreds will always be the same. Once the inbreds that give a superior hybrid have been identified, the hybrid seed can be reproduced indefinitely as long as the homogeneity of the inbred parents is maintained.

Controlling Self-Pollination

Canola varieties are mainly self-pollinated; therefore, self-pollination of the parental varieties must be controlled to make hybrid development feasible. In developing improved new *Brassica* hybrid varieties, breeders may use self-incompatible (SI), cytoplasmic male sterile (CMS) or nuclear male sterile (NMS) *Brassica* plants as the female parent. In using these plants, breeders are attempting to improve the efficiency of seed production and the quality of the $F_1$ hybrids and to reduce the breeding costs. When hybridization is conducted without using SI, CMS or NMS plants, it is more difficult to obtain and isolate the desired traits in the progeny ($F_1$ generation) because the parents are capable of undergoing both cross-pollination and self-pollination. If one of the parents is a SI, CMS or NMS plant that is incapable of producing pollen, only cross pollination will occur. By eliminating the pollen of one parental variety in a cross, a plant breeder is assured of obtaining hybrid seed of uniform quality, provided that the parents are of uniform quality and the breeder conducts a single cross.

In one instance, production of $F_1$ hybrids includes crossing a CMS *Brassica* female parent with a pollen-producing male *Brassica* parent. To reproduce effectively, however, the male parent of the $F_1$ hybrid must have a fertility restorer gene (Rf gene). The presence of an Rf gene means that the $F_1$ generation will not be completely or partially sterile, so that either self-pollination or cross pollination may occur. Self-pollination of the $F_1$ generation to produce several subsequent generations is important to ensure that a desired trait is heritable and stable and that a new variety has been isolated.

An example of a *Brassica* plant which is cytoplasmic male sterile and used for breeding is Ogura (OGU) cytoplasmic male sterile (Pellan-Delourme, et al., 1987). A fertility restorer for Ogura cytoplasmic male sterile plants has been transferred from *Raphanus sativus* (radish) to *Brassica* by Instit. National de Recherche Agricole (INRA) in Rennes, France (Pelletier, et al., 1987). The OGU INRA restorer gene, Rf1 originating from radish, is described in WO 92/05251 and in Delourme, et al., (1991). Improved versions of this restorer have been developed. For example, see WO98/27806, oilseed *brassica* containing an improved fertility restorer gene for Ogura cytoplasmic male sterility, which is hereby incorporated by reference.

Other sources and refinements of CMS sterility in canola include the Polima cytoplasmic male sterile plant, as well as those of U.S. Pat. No. 5,789,566, DNA sequence imparting cytoplasmic male sterility, mitochondrial genome, nuclear genome, mitochondria and plant containing said sequence and process for the preparation of hybrids; U.S. Pat. No. 5,973,233 Cytoplasmic male sterility system production canola hybrids; and WO97/02737 Cytoplasmic male sterility system producing canola hybrids; EP Patent Application Number 0 599042A Methods for introducing a fertility restorer gene and for producing F1 hybrids of *Brassica* plants thereby; U.S. Pat. No. 6,229,072 Cytoplasmic male sterility system production canola hybrids; U.S. Pat. No. 4,658,085 Hybridization using cytoplasmic male sterility, cytoplasmic herbicide tolerance, and herbicide tolerance from nuclear genes; all of which are incorporated herein for this purpose.

Promising advanced breeding lines commonly are tested and compared to appropriate standards in environments representative of the commercial target area(s). The best lines are candidates for new commercial lines; and those still deficient in a few traits may be used as parents to produce new populations for further selection.

Inbred Development—Female

The female parent is developed by crossing a male sterile version of variety NS6207 (A-line) with a maintainer line of variety NS6207 (B-line). The A and B lines are genetically alike except the A-line carries the OGU INRA cytoplasm, while the B-line carries the normal *B. napus* cytoplasm.

The B-line was developed using doubled haploidy method from a simple cross. The last crossing was completed in 2002 and the DH lines were extracted in 2003. These were evaluated in the field nursery in 2004 and 2005 for imidazolinone tolerance, early maturity, lodging resistance, high oil and protein, general vigor and uniformity. Backcrossing was carried out in the greenhouse to transfer the OGU INRA cytoplasm. Breeder Seed for the A line was bulked at BC7.

Inbred Development—Male

A male parent or restorer (R line) of variety NS6486 is designated NS6486MI. The restorer was developed using pedigree method from a three way cross where the last crossing was in 2004. The F2 bulk from the three-way cross was planted in the greenhouse for selfing and blackleg selection. The F3s were then were evaluated in Saskatoon nursery in 2005 for imidazolinone tolerance, general vigor, uniformity, maturity, oil %, protein %, total glucosinolates, total saturates, etc. Selected lines were selfed to produce F4. The harvested F4s were sent to Chile in 2005/2006 for F5 production. The F5s were evaluated in the 2006 nursery for similar traits as in 2005. From here, the selected lines was assigned new numbers and used in testcross production in Chile. The testcross hybrids were evaluated in 2007. Based on testcross performance a line was selected and was assigned a permanent number. Using this restorer line, hybrid 10N414I was produced and evaluated in two years of replicated yield trials. Pure inbred seed from the selected F5s was increased and then used to produce hybrid seed. The hybrid 10N414I was evaluated in 2011 Private trials.

Hybrid Development

45H76 (10N414I) is a fully restored spring *Brassica napus* hybrid with the Imidazolinone resistance, based on OGU INRA system developed in Saskatoon. It is a single cross hybrid produced by crossing a female parent (male sterile inbred-A line×maintainer inbred-B line) carrying the imidazolinone resistance genes by a restorer—male R line (also carrying the imidazolinone resistance genes), where A and B lines are genetically alike except the A line carries the OGU INRA cytoplasm, while the B line carries the normal *B. napus* cytoplasm.

A pollination control system and effective transfer of pollen from one parent to the other offers improved plant breeding and an effective method for producing hybrid canola seed and plants. For example, the Ogura cytoplasmic male sterility (CMS) system, developed via protoplast fusion between radish (*Raphanus sativus*) and rapeseed (*Brassica napus*), is one of the most frequently used methods of hybrid production. It provides stable expression of the male sterility trait (Ogura, 1968, Pelletier, et al., 1983) and an effective nuclear restorer gene (Heyn, 1976).

For most traits the true genotypic value may be masked by other confounding plant traits or environmental factors. One method for identifying a superior plant is to observe its performance relative to other experimental plants and to one or more widely grown standard varieties. If a single observation is inconclusive, replicated observations provide a better estimate of the genetic worth.

Proper testing should detect any major faults and establish the level of superiority or improvement over current varieties. In addition to showing superior performance, there must be a demand for a new variety that is compatible with industry standards or which creates a new market. The introduction of a new variety commonly will incur additional costs to the seed producer, the grower, the processor and the consumer, for special advertising and marketing, altered seed and commercial production practices, and new product utilization. The testing preceding release of a new variety should take into consideration research and development costs as well as technical superiority of the final variety. For seed-propagated varieties, it must be feasible to produce seed easily and economically.

These processes, which lead to the final step of marketing and distribution, usually take from approximately six to twelve years from the time the first cross is made. Therefore, the development of new varieties is a time-consuming process that requires precise forward planning, efficient use of resources, and a minimum of changes in direction.

Further, as a result of the advances in sterility systems, lines are developed that can be used as an open pollinated variety (i.e., a pureline cultivar sold to the grower for planting) and/or as a sterile inbred (female) used in the production of $F_1$ hybrid seed. In the latter case, favorable combining ability with a restorer (male) would be desirable. The resulting hybrid seed would then be sold to the grower for planting.

Combining ability of a line, as well as the performance of the line per se, is a factor in the selection of improved canola lines that may be used as inbreds. Combining ability refers to a line's contribution as a parent when crossed with other lines to form hybrids. The hybrids formed for the purpose of selecting superior lines are designated test crosses. One way of measuring combining ability is by using breeding values. Breeding values are based on the overall mean of a number of test crosses. This mean is then adjusted to remove environmental effects and it is adjusted for known genetic relationships among the lines.

Hybrid seed production requires inactivation of pollen produced by the female parent. Incomplete inactivation of the pollen provides the potential for self-pollination. This inadvertently self-pollinated seed may be unintentionally harvested and packaged with hybrid seed. Similarly, because the male parent is grown next to the female parent in the field, there is also the potential that the male selfed seed could be unintentionally harvested and packaged with the hybrid seed. Once the seed from the hybrid bag is planted, it is possible to identify and select these self-pollinated plants. These self-pollinated plants will be genetically equivalent to one of the inbred lines used to produce the hybrid. Though the possibility of inbreds being included in hybrid seed bags exists, the occurrence is rare because much care is taken to avoid such inclusions. These self-pollinated plants can be identified and selected by one skilled in the art, through either visual or molecular methods.

*Brassica napus* canola plants, absent the use of sterility systems, are recognized to commonly be self-fertile with approximately 70 to 90 percent of the seed normally forming as the result of self-pollination. The percentage of cross pollination may be further enhanced when populations of recognized insect pollinators at a given growing site are greater. Thus open pollination is often used in commercial canola production.

Since canola variety 45H76 is a hybrid produced from substantially homogeneous parents, it can be reproduced by planting seeds of such parents, growing the resulting canola plants under controlled pollination conditions with adequate isolation so that cross-pollination occurs between the parents, and harvesting the resulting hybrid seed using conventional agronomic practices.

Locus Conversions of Canola Variety 45H76

45H76 represents a new base genetic line into which a new locus or trait may be introduced. Direct transformation and backcrossing represent two important methods that can be used to accomplish such an introgression. The term locus conversion is used to designate the product of such an introgression.

To select and develop a superior hybrid, it is necessary to identify and select genetically unique individuals that occur in a segregating population. The segregating population is the result of a combination of crossover events plus the independent assortment of specific combinations of alleles at many gene loci that results in specific and unique genotypes. Once such a variety is developed its value to society is substantial since it is important to advance the germplasm base as a whole in order to maintain or improve traits such as yield, disease resistance, pest resistance and plant performance in extreme weather conditions. Locus conversions are routinely used to add or modify one or a few traits of such a line and this further enhances its value and usefulness to society.

Backcrossing can be used to improve inbred varieties and a hybrid variety which is made using those inbreds. Backcrossing can be used to transfer a specific desirable trait from one variety, the donor parent, to an inbred called the recurrent parent which has overall good agronomic characteristics yet that lacks the desirable trait. This transfer of the desirable trait into an inbred with overall good agronomic characteristics can be accomplished by first crossing a recurrent parent to a donor parent (non-recurrent parent). The progeny of this cross is then mated back to the recurrent parent followed by selection in the resultant progeny for the desired trait to be transferred from the non-recurrent parent.

Traits may be used by those of ordinary skill in the art to characterize progeny. Traits are commonly evaluated at a significance level, such as a 1%, 5% or 10% significance level, when measured in plants grown in the same environmental conditions. For example, a locus conversion of 45H76 may be characterized as having essentially the same phenotypic traits as 45H76. The traits used for comparison may be those traits shown in any of Tables 1-6. Molecular markers can also be used during the breeding process for the selection of qualitative traits. For example, markers can be used to select plants that contain the alleles of interest during a backcrossing breeding program. The markers can also be used to select for the genome of the recurrent parent and against the genome of the donor parent. Using this procedure can minimize the amount of genome from the donor parent that remains in the selected plants.

A locus conversion of 45H76 will retain the genetic integrity of 45H76. A locus conversion of 45H76 will comprise at least 92%, 93%, 94%, 95%, 96%, 97%, 98% or 99% of the base genetics of 45H76. For example, a locus conversion of 45H76 can be developed when DNA sequences are introduced through backcrossing (Hallauer et al., 1988), with a parent of 45H76 utilized as the recurrent parent. Both naturally occurring and transgenic DNA sequences may be introduced through backcrossing techniques. A backcross conversion may produce a plant with a locus conversion in at least one or more backcrosses, including at least 2 crosses, at least 3 crosses, at least 4 crosses, at least 5 crosses and the like. Molecular marker assisted breeding or selection may be utilized to reduce the number of backcrosses necessary to achieve the backcross conversion. For example, see Openshaw, S. J. et al., Marker-assisted Selection in Backcross Breeding. In: Proceedings Symposium of the Analysis of Molecular Data, August 1994, Crop Science Society of America, Corvallis, Oreg., where it is demonstrated that a backcross conversion can be made in as few as two backcrosses.

Uses of Canola

Currently *Brassica napus* canola is being recognized as an increasingly important oilseed crop and a source of meal in many parts of the world. The oil as removed from the seeds commonly contains a lesser concentration of endogenously formed saturated fatty acids than other vegetable oils and is well suited for use in the production of salad oil or other food products or in cooking or frying applications. The oil also finds utility in industrial applications. Additionally, the meal component of the seeds can be used as a nutritious protein concentrate for livestock.

Canola oil has the lowest level of saturated fatty acids of all vegetable oils. "Canola" refers to rapeseed (*Brassica*) which (1) has an erucic acid ($C_{22:1}$) content of at most 2 percent by weight based on the total fatty acid content of a seed, preferably at most 0.5 percent by weight and most preferably essentially 0 percent by weight; and (2) produces, after crushing, an air-dried meal containing less than 30 micromoles (μmol) glucosinolates per gram of defatted (oil-free) meal. These types of rapeseed are distinguished by their edibility in comparison to more traditional varieties of the species.

Disease—*Sclerotinia*

*Sclerotinia* infects over 100 species of plants, including numerous economically important crops such as *Brassica* species, sunflowers, dry beans, soybeans, field peas, lentils, lettuce, and potatoes (Boland and Hall, 1994). *Sclerotinia sclerotiorum* is responsible for over 99% of *Sclerotinia* disease, while *Sclerotinia minor* produces less than 1% of the disease. *Sclerotinia* produces sclerotia, irregularly-shaped, dark overwintering bodies, which can endure in soil for four to five years. The sclerotia can germinate carpogenically or myceliogenically, depending on the environmental conditions and crop canopies. The two types of germination cause two distinct types of diseases. Sclerotia that germinate carpogenically produce apothecia and ascospores that infect above-ground tissues, resulting in stem blight, stalk rot, head rot, pod rot, white mold and blossom blight of plants. Sclerotia that germinate myceliogenically produce mycelia that infect root tissues, causing crown rot, root rot and basal stalk rot.

*Sclerotinia* causes *Sclerotinia* stem rot, also known as white mold, in *Brassica*, including canola. Canola is a type of *Brassica* having a low level of glucosinolates and erucic acid in the seed. The sclerotia germinate carpogenically in the summer, producing apothecia. The apothecia release wind-borne ascospores that travel up to one kilometer. The disease is favoured by moist soil conditions (at least 10 days at or near field capacity) and temperatures of 15-25° C., prior to and during canola flowering. The spores cannot infect leaves and stems directly; they must first land on flowers, fallen petals, and pollen on the stems and leaves. Petal age affects the efficiency of infection, with older petals more likely to result in infection (Heran, et al., 1999). The fungal spores use the flower parts as a food source as they germinate and infect the plant.

The severity of *Sclerotinia* in *Brassica* is variable, and is dependent on the time of infection and climatic conditions (Heran, et al., 1999). The disease is favored by cool temperatures and prolonged periods of precipitation. Temperatures between 20 and 25° C. and relative humidities of greater than 80% are required for optimal plant infection (Heran, et al., 1999). Losses ranging from 5 to 100% have been reported for individual fields (Manitoba Agriculture, Food and Rural Initiatives, 2004). On average, yield losses are estimated to be 0.4 to 0.5 times the *Sclerotinia sclerotiorum* Field Severity score, a rating based on both percentage infection and disease severity. More information is provided herein at Example 4. For example, if a field has 20% infection (20/100 plants infected), then the yield loss would be about 10% provided plants are dying prematurely due to the infection of the main stem (rating 5-SSFS=20%). If the plants are affected much less (rating 1-SSFS=4%), yield loss is reduced accordingly. Further, *Sclerotinia* can cause heavy losses in wet swaths. *Sclerotinia sclerotiorum* caused economic losses to canola growers in Minnesota and North Dakota of 17.3, 20.8, and 16.8 million dollars in 1999, 2000 and 2001, respectively (Bradley, et al. 2006). In Canada, this disease is extremely important in Southern Manitoba, parts of South Central Alberta and also in Eastern areas of Saskatchewan. Since weather plays an important role in development of this disease, its occurrence is irregular and unpredictable. Certain reports estimate about 0.8 to 1.3 million acres of canola being sprayed with fungicide in Southern Manitoba annually. The fungicide application costs about $25 per acre, which represents a significant cost for canola producers. Moreover, producers may decide to apply fungicide based on the weather forecast, while later changes in the weather pattern discourage disease development, resulting in wasted product, time, and fuel. Creation of *Sclerotinia* tolerant canola cultivars has been an important goal for many of the Canadian canola breeding organizations.

The symptoms of *Sclerotinia* infection usually develop several weeks after flowering begins. The plants develop pale-grey to white lesions, at or above the soil line and on upper branches and pods. The infections often develop where the leaf and the stem join because the infected petals lodge there. Once plants are infected, the mold continues to grow into the stem and invade healthy tissue. Infected stems appear bleached and tend to shred. Hard black fungal sclerotia develop within the infected stems, branches, or pods. Plants infected at flowering produce little or no seed. Plants with girdled stems wilt and ripen prematurely. Severely infected crops frequently lodge, shatter at swathing, and make swathing more time consuming. Infections can occur in all above-ground plant parts, especially in dense or lodged stands, where plant-to-plant contact facilitates the spread of infection. New sclerotia carry the disease over to the next season.

Conventional methods for control of *Sclerotinia* diseases include (a) chemical control, (b) disease resistance and (c) cultural control, each of which is described below.

(a) Fungicides such as benomyl, vinclozolin and iprodione remain the main method of control of *Sclerotinia* disease (Morall, et al., 1985; Tu, 1983). Recently, additional fungicidal formulations have been developed for use against *Sclerotinia*, including azoxystrobin, prothioconazole, and boscalid. (Johnson, 2005) However, use of fungicide is expensive and can be harmful to the user and environment. Further, resistance to some fungicides has occurred due to repeated use.

(b) In certain cultivars of bean, safflower, sunflower and soybean, some progress has been made in developing partial (incomplete) resistance. Partial resistance is often referred to as tolerance. However, success in developing partial resistance has been very limited, probably because partial physiological resistance is a multigene trait as demonstrated in bean (Fuller, et al., 1984). In addition to partial physiological resistance, some progress has been made to breed for morphological traits to avoid *Sclerotinia* infection, such as upright growth habit, lodging resistance and narrow canopy. For example, bean plants with partial physiological resistance and with an upright stature, narrow canopy and indeterminate growth habit were best able to avoid *Sclerotinia* (Saindon, et al., 1993). Early maturing cultivars of safflower showed good field resistance to *Sclerotinia*. Finally, in soybean, cultivar characteristics such as height, early maturity and great lodging resistance result in less disease, primarily because of a reduction of favorable microclimate conditions for the disease. (Boland and Hall, 1987; Buzzell, et al. 1993)

(c) Cultural practices, such as using pathogen-free or fungicide-treated seed, increasing row spacing, decreasing seeding rate to reduce secondary spread of the disease, and burying sclerotia to prevent carpogenic germination, may reduce *Sclerotinia* disease but not effectively control the disease.

Canola genotypes can be susceptible to *Sclerotinia* stem rot. This includes all known spring petalled genotypes of canola quality. There is also no resistance to *Sclerotinia* in Australian canola varieties. (Hind-Lanoiselet, et al. 2004). Some varieties with certain morphological traits are better able to withstand *Sclerotinia* infection. For example, Polish varieties (*Brassica rapa*) have lighter canopies and seem to have much lower infection levels. In addition, petal-less varieties (apetalous varieties) avoid *Sclerotinia* infection to a greater extent (Okuyama, et al., 1995; Fu, 1990). Other examples of morphological traits which confer a degree of reduced field susceptibility in *Brassica* genotypes include increased standability, reduced petal retention, branching (less compact and/or higher), and early leaf abscission. Jurke and Fernando, (2003) screened eleven canola genotypes for *Sclerotinia* disease incidence. Significant variation in disease incidence was explained by plant morphology, and the difference in petal retention was identified as the most important factor. However, these morphological traits alone do not confer resistance to *Sclerotinia*, and all canola products in Canada are considered susceptible to *Sclerotinia*.

Winter canola genotypes are also susceptible to *Sclerotinia*. In Germany, for example, no *Sclerotinia*-resistant varieties are available. (Specht, 2005) The widely-grown German variety Express is considered susceptible to moderately susceptible and belongs to the group of less susceptible varieties/hybrids.

Spraying with fungicide is the only means of controlling *Sclerotinia* in canola crops grown under disease-favorable conditions at flowering. Typical fungicides used for controlling *Sclerotinia* on *Brassica* include Rovral™/Proline™ from Bayer and Ronilan™/Lance™ from BASF. The active ingredient in Lance™ is Boscalid, and it is marketed as Endura™ in the United States. The fungicide should be applied before symptoms of stem rot are visible and usually at the 20-30% bloom stage of the crop. If infection is already evident, there is no use in applying fungicide as it is too late to have an effect. Accordingly, growers must assess their fields for disease risk to decide whether to apply a fungicide. This can be done by using a government provided checklist or by using a petal testing kit. Either method is cumbersome and prone to errors. (Hind-Lanoiselet, 2004; Johnson, 2005)

Numerous efforts have been made to develop *Sclerotinia* resistant *Brassica* plants. Built-in resistance would be more convenient, economical, and environmentally-friendly than controlling *Sclerotinia* by application of fungicides. Since the trait is polygenic it would be stable and not prone to loss of efficacy, as fungicides may be.

Characteristics of 45H76

Homogenous and reproducible canola hybrids are useful for the production of a commercial crop on a reliable basis. There are a number of analytical methods available to determine the phenotypic stability of a canola hybrid.

The oldest and most traditional method of analysis is the observation of phenotypic traits. The data are usually collected in field experiments over the life of the canola plants to be examined. Phenotypic characteristics most often are observed for traits associated with seed yield, seed oil content, seed protein content, fatty acid composition of oil, glucosinolate content of meal, growth habit, lodging resistance, plant height, shatter resistance, etc.

In addition to phenotypic observations, the genotype of a plant can also be examined. A plant's genotype can be used to identify plants of the same variety or a related variety. For example, the genotype can be used to determine the pedigree of a plant. There are many laboratory-based techniques available for the analysis, comparison and characterization of plant genotype; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) which are also referred to as Microsatellites, and Single Nucleotide Polymorphisms (SNPs).

The variety of the present discovery has shown uniformity and stability for all traits, as described in the following variety description information. The variety has been increased with continued observation for uniformity.

45H76 is a medium maturing, high yielding Imidazolinone tolerant *Brassica napus* canola hybrid having resistant (R) rating for blackleg and resistant (R) rating for *Fusarium* wilt. Its oil content is similar to the WCC/RRC checks. Its protein and chlorophyll contents are higher than the checks.

Table 1 provides data on morphological, agronomic, and quality traits for 45H76 and canola variety 46H75. When preparing the detailed phenotypic information that follows, plants of the new 45H76 variety were observed while being grown using conventional agronomic practices. For comparative purposes, canola plants of canola varieties, 46H75 was similarly grown in a replicated experiment.

Observations were recorded on various morphological traits for the hybrid 45H76 and comparative check cultivars. (See Table 1).

Hybrid 45H76 can be advantageously used in accordance with the breeding methods described herein and those known in the art to produce hybrids and other progeny plants retaining desired trait combinations of 45H76. This discovery is thus also directed to methods for producing a canola plant by crossing a first parent canola plant with a second parent canola plant wherein either the first or second parent canola plant is canola variety 45H76. Further, both first and second parent canola plants can come from the canola variety 45H76. Either the first or the second parent plant may be male sterile.

Still further, this discovery also is directed to methods for producing a 45H76-derived canola plant by crossing canola variety 45H76 with a second canola plant and growing the progeny seed, and repeating the crossing and growing steps with the canola 45H76-derived plant from 1 to 2 times, 1 to 3 times, 1 to 4 times, or 1 to 5 times. Thus, any such methods using the canola variety 45H76 are part of this discovery: open pollination, selfing, backcrosses, hybrid production, crosses to populations, and the like. All plants produced using canola variety 45H76 as a parent are within the scope of this discovery, including plants derived from canola variety 45H76. This includes canola lines derived from 45H76 which include components for either male sterility or for restoration of fertility. Advantageously, the canola variety is used in crosses with other, different, canola plants to produce first generation ($F_1$) canola hybrid seeds and plants with superior characteristics.

The discovery also includes a single-gene conversion of 45H76. A single-gene conversion occurs when DNA sequences are introduced through traditional (non-transformation) breeding techniques, such as backcrossing. DNA sequences, whether naturally occurring or transgenes, may be introduced using these traditional breeding techniques. Desired traits transferred through this process include, but are not limited to, fertility restoration, fatty acid profile modification, other nutritional enhancements, industrial enhancements, disease resistance, insect resistance, herbicide resistance and yield enhancements. The trait of interest is transferred from the donor parent to the recurrent parent, in this case, the canola plant disclosed herein. Single-gene traits may result from the transfer of either a dominant allele or a recessive allele. Selection of progeny containing the trait of interest is done by direct selection for a trait associated with a dominant allele. Selection of progeny for a trait that is transferred via a recessive allele will require growing and selfing the first backcross to determine which plants carry the recessive alleles. Recessive traits may require additional progeny testing in successive backcross generations to determine the presence of the gene of interest.

It should be understood that the canola variety of the discovery can, through routine manipulation by cytoplasmic genes, nuclear genes, or other factors, be produced in a male-sterile or restorer form as described in the references discussed earlier. Such embodiments are also within the scope of the present claims. Canola variety 45H76 can be manipulated to be male sterile by any of a number of methods known in the art, including by the use of mechanical methods, chemical methods, self-incompatibility (SI), cytoplasmic male sterility (CMS) (either Ogura or another system), or nuclear male sterility (NMS). The term "manipulated to be male sterile" refers to the use of any available techniques to produce a male sterile version of canola variety 45H76. The male sterility may be either partial or complete male sterility. This discovery is also directed to F1 hybrid seed and plants produced by the use of Canola variety 45H76. Canola variety 45H76 can also further comprise a component for fertility restoration of a male sterile plant, such as an Rf restorer gene. In this case, canola variety 45H76 could then be used as the male plant in hybrid seed production.

This discovery is also directed to the use of 45H76 in tissue culture. As used herein, the term plant includes plant protoplasts, plant cell tissue cultures from which canola plants can be regenerated, plant calli, plant clumps, and plant cells that are intact in plants or parts of plants, such as embryos, pollen, ovules, seeds, flowers, kernels, ears, cobs, leaves, husks, stalks, roots, root tips, anthers, silk and the like. Pauls, et al., (2006) (*Canadian J of Botany* 84(4):668-678) confirmed that tissue culture as well as microspore culture for regeneration of canola plants can be accomplished successfully. Chuong, et al., (1985) "A Simple Culture Method for *Brassica* Hypocotyl Protoplasts", *Plant Cell Reports* 4:4-6; Barsby, et al., (Spring 1996) "A Rapid and Efficient Alternative Procedure for the Regeneration of Plants from Hypocotyl Protoplasts of *Brassica napus*", *Plant Cell Reports*; Kartha, et al., (1974) "In vitro Plant Formation from Stem Explants of Rape", *Physiol. Plant* 31:217-220; Narasimhulu, et al., (Spring 1988) "Species Specific Shoot Regeneration Response of Cotyledonary Explants of *Brassicas*", *Plant Cell Reports*; Swanson, (1990) "Microspore Culture in *Brassica*", *Methods in Molecular Biology* 6(17):159; "Cell Culture techniques and Canola improvement" *J. Am. Oil Chem. Soc.* 66(4):455-56 (1989). Thus, it is clear from the literature that the state of the art is such that these methods of obtaining plants are, and were, "conventional" in the sense that they are routinely used and have a very high rate of success.

The utility of canola variety 45H76 also extends to crosses with other species. Commonly, suitable species will be of the family *Brassicae*.

The advent of new molecular biological techniques has allowed the isolation and characterization of genetic elements with specific functions, such as encoding specific protein products. Scientists in the field of plant biology developed a strong interest in engineering the genome of plants to contain and express foreign genetic elements, or additional, or modified versions of native or endogenous genetic elements in order to alter the traits of a plant in a specific manner. Any DNA sequences, whether from a different species, or from the same species that are inserted into the genome using transformation are referred to herein collectively as "transgenes". Over the last fifteen to twenty years several methods for producing transgenic plants have been developed, and the present discovery, in particular embodiments, also relates to transformed versions of the claimed canola variety 45H76.

Numerous methods for plant transformation have been developed, including biological and physical plant transformation protocols. See, for example, Miki, et al., "Procedures for Introducing Foreign DNA into Plants" in *Methods in Plant Molecular Biology and Biotechnology*, Glick, and Genetic Transformation for the improvement of Canola World Conf, Biotechnol. Fats and Oils Ind. 43-46 (1988). In addition, expression vectors and in vitro culture methods for plant cell or tissue transformation and regeneration of plants are available. See, for example, Gruber, et al., "Vectors for Plant Transformation" in *Methods in Plant Molecular Biol-* ogy and Biotechnology, Glick and Thompson, Eds. (CRC Press, Inc., Boca Raton, 1993) pages 89-119.

The most prevalent types of plant transformation involve the construction of an expression vector. Such a vector comprises a DNA sequence that contains a gene under the control of or operatively linked to a regulatory element, for example a promoter. The vector may contain one or more genes and one or more regulatory elements.

A genetic trait which has been engineered into a particular canola plant using transformation techniques could be moved into another line using traditional breeding techniques that are well known in the plant breeding arts. For example, a backcrossing approach could be used to move a transgene from a transformed canola plant to an elite inbred line and the resulting progeny would comprise a transgene. Also, if an inbred line was used for the transformation then the transgenic plants could be crossed to a different line in order to produce a transgenic hybrid canola plant. As used herein, "crossing" can refer to a simple X by Y cross, or the process of backcrossing, depending on the context. Various genetic elements can be introduced into the plant genome using transformation. These elements include but are not limited to genes; coding sequences; inducible, constitutive, and tissue specific promoters; enhancing sequences; and signal and targeting sequences. See, U.S. Pat. No. 6,222,101 which is herein incorporated by reference.

With transgenic plants according to the present discovery, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, (1981) *Anal. Biochem.* 114:92-96.

A genetic map can be generated, primarily via conventional Restriction Fragment Length Polymorphisms (RFLP), Polymerase Chain Reaction (PCR) analysis, Simple Sequence Repeats (SSR), and Single Nucleotide Polymorphisms (SNPs), which identifies the approximate chromosomal location of the integrated DNA molecule coding for the foreign protein. For exemplary methodologies in this regard, see, Glick and Thompson, METHODS IN PLANT MOLECULAR BIOLOGY AND BIOTECHNOLOGY 269-284 (CRC Press, Boca Raton, 1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR, SNP, and sequencing, all of which are conventional techniques.

Likewise, by means of the present discovery, plants can be genetically engineered to express various phenotypes of agronomic interest. Exemplary transgenes implicated in this regard include, but are not limited to, those categorized below.

1. Genes that Confer Resistance to Pests or Disease and that Encode:

(A) Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. See, for example Jones, et al., (1994) *Science* 266:789 (cloning of the tomato Cf-9 gene for resistance to *Cladosporium fulvum*); Martin, et al., (1993) *Science* 262: 1432 (tomato Pto gene for resistance to *Pseudomonas syringae* pv. tomato encodes a protein kinase); Mindrinos, et al., (1994) *Cell* 78:1089 (*Arabidopsis* RSP2 gene for resistance to *Pseudomonas syringae*); McDowell and Woffenden, (2003) *Trends Biotechnol.* 21(4):178-83 and Toyoda, et al., (2002) *Transgenic Res.* 11(6):567-82. A plant resistant to a disease is one that is more resistant to a pathogen as compared to the wild type plant.

(B) A gene conferring resistance to fungal pathogens, such as oxalate oxidase or oxalate decarboxylase (Zhou, et al., (1998) *Pl. Physiol.* 117(1):33-41).

(C) A *Bacillus thuringiensis* (Bt) protein, a derivative thereof or a synthetic polypeptide modeled thereon. See, for example, Geiser, et al., (1986) *Gene* 48:109, who disclose the cloning and nucleotide sequence of a Bt delta-endotoxin gene. Moreover, DNA molecules encoding delta-endotoxin genes can be purchased from American Type Culture Collection (Manassas, Va.), for example, under ATCC Accession Numbers. 40098, 67136, 31995 and 31998. Other examples of *Bacillus thuringiensis* transgenes being genetically engineered are given in the following patents and patent applications and hereby are incorporated by reference for this purpose: U.S. Pat. Nos. 5,188,960; 5,689,052; 5,880, 275; WO 91/114778; WO 99/31248; WO 01/12731; WO 99/24581; WO 97/40162 and U.S. application Ser. Nos. 10/032,717; 10/414,637; and 10/606,320.

(D) An insect-specific hormone or pheromone such as an ecdysteroid and juvenile hormone, a variant thereof, a mimetic based thereon, or an antagonist or agonist thereof. See, for example, the disclosure by Hammock, et al., (1990) *Nature* 344:458, of baculovirus expression of cloned juvenile hormone esterase, an inactivator of juvenile hormone.

(E) An insect-specific peptide which, upon expression, disrupts the physiology of the affected pest. For example, see the disclosures of Regan, (1994) *J. Biol. Chem.* 269:9 (expression cloning yields DNA coding for insect diuretic hormone receptor) and Pratt, et al., (1989) *Biochem. Biophys. Res. Comm.* 163:1243 (an allostatin is identified in *Diploptera puntata*); Chattopadhyay, et al., (2004) *Critical Reviews in Microbiology* 30(1):33-54 2004; Zjawiony, (2004) *J Nat Prod* 67(2):300-310; Carlini and Grossi-de-Sa, (2002) *Toxicon* 40(11):1515-1539; Ussuf, et al., (2001) *Curr Sci.* 80(7):847-853 and Vasconcelos and Oliveira, (2004) *Toxicon* 44(4):385-403. See also, U.S. Pat. No. 5,266,317 to Tomalski, et al., who disclose genes encoding insect-specific, paralytic neurotoxins.

(F) An enzyme responsible for a hyperaccumulation of a monterpene, a sesquiterpene, a steroid, hydroxamic acid, a phenylpropanoid derivative or another non-protein molecule with insecticidal activity.

(G) An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT Application Number WO 93/02197 in the name of Scott, et al., which discloses the nucleotide sequence of a callase gene. DNA molecules which contain chitinase-encoding sequences can be obtained, for example, from the ATCC under Accession Numbers 39637 and 67152. See also, Kramer, et al., (1993) *Insect Biochem. Molec. Biol.* 23:691, who teach the nucleotide sequence of a cDNA encoding tobacco hookworm chitinase, and Kawalleck et al., (1993) *Plant Molec. Biol.* 21:673, who provide the nucleotide sequence of the parsley ubi4-2 polyubiquitin gene, U.S. patent application Ser. Nos. 10/389,432, 10/692,367 and U.S. Pat. No. 6,563,020.

(H) A molecule that stimulates signal transduction. For example, see the disclosure by Botella, et al., (1994) *Plant Molec. Biol.* 24:757, of nucleotide sequences for mung bean calmodulin cDNA clones, and Griess, et al., (1994) *Plant Physiol.* 104:1467, who provide the nucleotide sequence of a maize calmodulin cDNA clone.

(I) A hydrophobic moment peptide. See, PCT Application Number WO95/16776 and U.S. Pat. No. 5,580,852 (disclosure of peptide derivatives of Tachyplesin which inhibit fungal plant pathogens) and PCT Application Number WO95/18855 and U.S. Pat. No. 5,607,914 (teaches synthetic antimicrobial peptides that confer disease resistance), the respective contents of which are hereby incorporated by reference for this purpose.

(J) A membrane permease, a channel former or a channel blocker. For example, see the disclosure by Jaynes, et al., (1993) *Plant Sci.* 89:43, of heterologous expression of a cecropin-beta lytic peptide analog to render transgenic tobacco plants resistant to *Pseudomonas solanacearum.*

(K) A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy, et al., (1990) *Ann. Rev. Phytopathol.* 28:451. Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

(L) An insect-specific antibody or an immunotoxin derived therefrom. Thus, an antibody targeted to a critical metabolic function in the insect gut would inactivate an affected enzyme, killing the insect. Cf. Taylor, et al., Abstract #497, SEVENTH INT'L SYMPOSIUM ON MOLECULAR PLANT-MICROBE INTERACTIONS (Edinburgh, Scotland, 1994) (enzymatic inactivation in transgenic tobacco via production of single-chain antibody fragments).

(M) A virus-specific antibody. See, for example, Tavladoraki, et al., (1993) *Nature* 366:469, who show that transgenic plants expressing recombinant antibody genes are protected from virus attack.

(N) A developmental-arrestive protein produced in nature by a pathogen or a parasite. Thus, fungal endo alpha-1,4-D-polygalacturonases facilitate fungal colonization and plant nutrient release by solubilizing plant cell wall homo-alpha-1,4-D-galacturonase. See, Lamb, et al., (1992) *Bio/Technology* 10:1436. The cloning and characterization of a gene which encodes a bean endopolygalacturonase-inhibiting protein is described by Toubart, et al., (1992) *Plant J.* 2:367.

(O) A developmental-arrestive protein produced in nature by a plant. For example, Logemann, et al., (1992) *Bio/Technology* 10:305, have shown that transgenic plants expressing the barley ribosome-inactivating gene have an increased resistance to fungal disease.

(P) Genes involved in the Systemic Acquired Resistance (SAR) Response and/or the pathogenesis related genes. Briggs, (1995) *Current Biology* 5(2):128-131, Pieterse and Van Loon, (2004) *Curr. Opin. Plant Bio* 7(4):456-64 and Somssich, (2003) *Cell* 113(7):815-6.

(Q) Antifungal genes (Cornelissen and Melchers, (1993) *Pl. Physiol.* 101:709-712 and Parijs, et al., (1991) *Planta* 183:258-264 and Bushnell, et al., (1998) *Can. J. of Plant Path.* 20(2):137-149. Also see, U.S. patent application Ser. No. 09/950,933.

(R) Detoxification genes, such as for fumonisin, beauvericin, moniliformin and zearalenone and their structurally related derivatives. For example, see, U.S. Pat. No. 5,792,931.

(S) Cystatin and cysteine proteinase inhibitors. See, U.S. patent application Ser. No. 10/947,979.

(T) Defensin genes. See, WO03/000863 and U.S. patent application Ser. No. 10/178,213.

(U) Genes that confer resistance to *Phytophthora* Root Rot, such as the *Brassica* equivalents of the Rps 1, Rps 1-a, Rps 1-b, Rps 1-c, Rps 1-d, Rps 1-e, Rps 1-k, Rps 2, Rps 3-a, Rps 3-b, Rps 3-c, Rps 4, Rps 5, Rps 6, Rps 7 and other Rps genes. See, for example, Shoemaker, et al, (1995) *Phytophthora* Root Rot Resistance Gene Mapping in Soybean, Plant Genome IV Conference, San Diego, Calif.

2. Genes that Confer Resistance to a Herbicide, for Example:

(A) A herbicide that inhibits the growing point or meristem, such as an imidazalinone or a sulfonylurea. Exemplary genes in this category code for mutant ALS and AHAS enzyme as described, for example, by Lee, et al., (1988) *EMBO J.* 7:1241, and Miki, et al., (1990) *Theor. Appl. Genet.* 80:449, respectively. See also, U.S. Pat. Nos. 5,605,011; 5,013,659; 5,141,870; 5,767,361; 5,731,180; 5,304,732; 4,761,373; 5,331,107; 5,928,937 and 5,378,824; and international publication WO 96/33270, which are incorporated herein by reference for this purpose.

(B) Glyphosate (resistance imparted by mutant 5-enolpyruvl-3-phoshikimate synthase (EPSP) and aroA genes, respectively) and other phosphono compounds such as glufosinate (phosphinothricin acetyl transferase, PAT) and *Streptomyces hygroscopicus* phosphinothricin-acetyl transferase, bar, genes), and pyridinoxy or phenoxy propionic acids and cycloshexones (ACCase inhibitor-encoding genes). See, for example, U.S. Pat. No. 4,940,835 to Shah, et al., which discloses the nucleotide sequence of a form of EPSP which can confer glyphosate resistance. See also, U.S. Pat. No. 7,405,074, and related applications, which disclose compositions and means for providing glyphosate resistance. U.S. Pat. No. 5,627,061 to Barry, et al., also describes genes encoding EPSPS enzymes. See also, U.S. Pat. Nos. 6,566,587; 6,338,961; 6,248,876 B1; 6,040,497; 5,804,425; 5,633,435; 5,145,783; 4,971,908; 5,312,910; 5,188,642; 4,940,835; 5,866,775; 6,225,114 B1; 6,130,366; 5,310,667; 4,535,060; 4,769,061; 5,633,448; 5,510,471; Re. 36,449; RE 37,287 E; and 5,491,288; and international publications EP1173580; WO 01/66704; EP1173581 and EP1173582, which are incorporated herein by reference for this purpose. A DNA molecule encoding a mutant aroA gene can be obtained under ATCC Accession Number 39256, and the nucleotide sequence of the mutant gene is disclosed in U.S. Pat. No. 4,769,061 to Comai. European Patent Application Number 0 333 033 to Kumada, et al., and U.S. Pat. No. 4,975,374 to Goodman, et al., disclose nucleotide sequences of glutamine synthetase genes which confer resistance to herbicides such as L-phosphinothricin. The nucleotide sequence of a phosphinothricin-acetyl-transferase gene is provided in European Application Number 0 242 246 to Leemans, et al., De Greef, et al., (1989) *Bio/Technology* 7:61, describe the production of transgenic plants that express chimeric bar genes coding for phosphinothricin acetyl transferase activity. See also, U.S. Pat. Nos. 5,969,213; 5,489,520; 5,550,318; 5,874,265; 5,919,675; 5,561,236; 5,648,477; 5,646,024; 6,177,616 B1 and 5,879,903, which are incorporated herein by reference for this purpose. Exemplary of genes conferring resistance to phenoxy propionic acids and cycloshexones, such as sethoxydim and haloxyfop, are the Acc1-S1, Acc1-S2 and Acc1-S3 genes described by Marshall, et al., (1992) *Theor. Appl. Genet.* 83:435. See also, U.S. Pat. Nos. 5,188,642; 5,352,605; 5,530,196; 5,633,435; 5,717,084; 5,728,925; 5,804,425 and Canadian Patent Number 1,313,830, which are incorporated herein by reference for this purpose.

(C) A herbicide that inhibits photosynthesis, such as a triazine (psbA and gs+ genes) and a benzonitrile (nitrilase gene). Przibilla, et al., (1991) *Plant Cell* 3:169, describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Numbers 53435, 67441 and 67442. Cloning and expression of DNA coding for a glutathione S-transferase is described by Hayes, et al., (1992) *Biochem. J.* 285:173.

(D) Acetohydroxy acid synthase, which has been found to make plants that express this enzyme resistant to multiple types of herbicides, has been introduced into a variety of plants (see, e.g., Hattori, et al., (1995) *Mol Gen Genet* 246:419). Other genes that confer tolerance to herbicides include: a gene encoding a chimeric protein of rat cytochrome P4507A1 and yeast NADPH-cytochrome P450 oxidoreductase (Shiota, et al., (1994) *Plant Physiol* 106:17), genes for glutathione reductase and superoxide dismutase (Aono, et al., (1995) *Plant Cell Physiol* 36:1687, and genes for various phosphotransferases (Datta, et al., (1992) *Plant Mol Biol* 20:619).

(E) Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306 B1; 6,282,837 B1; and 5,767,373; and international publication WO 01/12825, which are incorporated herein by reference for this purpose.

3. Transgenes that Confer or Contribute to an Altered Grain Characteristic, Such as:

(A) Altered fatty acids, for example, by
(1) Down-regulation of stearoyl-ACP desaturase to increase stearic acid content of the plant. See, Knultzon, et al., (1992) *Proc. Natl. Acad. Sci. USA* 89:2624 and WO99/64579 (Genes for Desaturases to Alter Lipid Profiles in Corn),
(2) Elevating oleic acid via FAD-2 gene modification and/or decreasing linolenic acid via FAD-3 gene modification (see, U.S. Pat. Nos. 6,063,947; 6,323,392; 6,372,965 and WO 93/11245),
(3) Altering conjugated linolenic or linoleic acid content, such as in WO 01/12800,
(4) Altering LEC1, AGP, Dek1, Superal1, mi1ps, various Ipa genes such as Ipa1, Ipa3, hpt or hggt. For example, see WO 02/42424, WO 98/22604, WO 03/011015, U.S. Pat. Nos. 6,423,886, 6,197,561, 6,825,397, US Patent Application Publication Numbers 2003/0079247, 2003/0204870, WO02/057439, WO03/011015 and Rivera-Madrid, et al., (1995) *Proc. Natl. Acad. Sci.* 92:5620-5624.

(B) Altered phosphate content, for example, by the
(1) Introduction of a phytase-encoding gene would enhance breakdown of phytate, adding more free phosphate to the transformed plant. For example, see, Van Hartingsveldt, et al., (1993) *Gene* 127:87, for a disclosure of the nucleotide sequence of an *Aspergillus niger* phytase gene.
(2) Up-regulation of a gene that reduces phytate content. In maize, this, for example, could be accomplished, by cloning and then re-introducing DNA associated with one or more of the alleles, such as the LPA alleles, identified in maize mutants characterized by low levels of phytic acid, such as in Raboy, et al., (1990) *Maydica* 35:383 and/or by altering inositol kinase activity as in WO 02/059324, US Patent Application Publication Number 2003/0009011, WO 03/027243, US Patent Application Publication Number 2003/0079247, WO 99/05298, U.S. Pat. Nos. 6,197,561, 6,291,224, 6,391,348, WO2002/059324, US Patent Application Publication Number 2003/0079247, WO98/45448, WO99/55882, WO01/04147.

(C) Altered carbohydrates effected, for example, by altering a gene for an enzyme that affects the branching pattern of starch, a gene altering thioredoxin. (See, U.S. Pat. No. 6,531,648). See, Shiroza, et al., (1988) *J. Bacteriol* 170:810 (nucleotide sequence of *Streptococcus mutans* fructosyltransferase gene), Steinmetz, et al., (1985) *Mol. Gen. Genet.* 200:220 (nucleotide sequence of *Bacillus subtilis* levansucrase gene), Pen, et al., (1992) *Bio/Technology* 10:292 (production of transgenic plants that express *Bacillus licheniformis* alpha-amylase), Elliot, et al., (1993) *Plant Molec Biol* 21:515 (nucleotide sequences of tomato invertase genes), Sogaard, et al., (1993) *J. Biol. Chem.* 268:22480 (site-directed mutagenesis of barley alpha-amylase gene) and Fisher, et al., (1993) *Plant Physiol* 102:1045 (maize endosperm starch branching enzyme II), WO 99/10498 (improved digestibility and/or starch extraction through modification of UDP-D-xylose 4-epimerase, Fragile 1 and 2, Ref1, HCHL, C4H), U.S. Pat. No. 6,232,529 (method of producing high oil seed by modification of starch levels (AGP)). The fatty acid modification genes mentioned above may also be used to affect starch content and/or composition through the interrelationship of the starch and oil pathways.

(D) Altered antioxidant content or composition, such as alteration of tocopherol or tocotrienols. For example, see, U.S. Pat. No. 6,787,683, US Patent Application Publication Number 2004/0034886 and WO 00/68393 involving the manipulation of antioxidant levels through alteration of a phytl prenyl transferase (ppt), WO 03/082899 through alteration of a homogentisate geranyl geranyl transferase (hggt).

(E) Altered essential seed amino acids. For example, see, U.S. Pat. No. 6,127,600 (method of increasing accumulation of essential amino acids in seeds), U.S. Pat. No. 6,080,913 (binary methods of increasing accumulation of essential amino acids in seeds), U.S. Pat. No. 5,990,389 (high lysine), WO99/40209 (alteration of amino acid compositions in seeds), WO99/29882 (methods for altering amino acid content of proteins), U.S. Pat. No. 5,850,016 (alteration of amino acid compositions in seeds), WO98/20133 (proteins with enhanced levels of essential amino acids), U.S. Pat. No. 5,885,802 (high methionine), U.S. Pat. No. 5,885,801 (high threonine), U.S. Pat. No. 6,664,445 (plant amino acid biosynthetic enzymes), U.S. Pat. No. 6,459,019 (increased lysine and threonine), U.S. Pat. No. 6,441,274 (plant tryptophan synthase beta subunit), U.S. Pat. No. 6,346,403 (methionine metabolic enzymes), U.S. Pat. No. 5,939,599 (high sulfur), U.S. Pat. No. 5,912,414 (increased methionine), WO98/56935 (plant amino acid biosynthetic enzymes), WO98/45458 (engineered seed protein having higher percentage of essential amino acids), WO98/42831 (increased lysine), U.S. Pat. No. 5,633,436 (increasing sulfur amino acid content), U.S. Pat. No. 5,559,223 (synthetic storage proteins with defined structure containing programmable levels of essential amino acids for improvement of the nutritional value of plants), WO96/01905 (increased threonine), WO95/15392 (increased lysine), US Patent Application Publication Number 2003/0163838, US Patent Application Publication Number 2003/0150014, US Patent Application Publication Number 2004/0068767, U.S. Pat. No. 6,803,498, WO01/79516, and WO00/09706 (Ces A: cellulose synthase), U.S. Pat. No. 6,194,638 (hemicellulose), U.S. Pat. No. 6,399,859 and US Patent Application Publication Number 2004/0025203 (UDPGdH), U.S. Pat. No. 6,194,638 (RGP).

4. Genes that Control Pollination, Hybrid Seed Production, or Male-Sterility:

There are several methods of conferring genetic male sterility available, such as multiple mutant genes at separate locations within the genome that confer male sterility, as disclosed in U.S. Pat. Nos. 4,654,465 and 4,727,219 to Brar, et al., and chromosomal translocations as described by Patterson in U.S. Pat. Nos. 3,861,709 and 3,710,511. In addition to these methods, Albertsen, et al., U.S. Pat. No. 5,432,068, describe a system of nuclear male sterility which includes: identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing, or turning "on", the promoter, which in turn allows the gene that confers male fertility to be transcribed.

(A) Introduction of a deacetylase gene under the control of a tapetum-specific promoter and with the application of the chemical N—Ac-PPT (WO 01/29237).

(B) Introduction of various stamen-specific promoters (WO 92/13956, WO 92/13957).

(C) Introduction of the barnase and the barstar gene (Paul, et al., (1992) *Plant Mol. Biol.* 19:611-622).

For additional examples of nuclear male and female sterility systems and genes, see also, U.S. Pat. Nos. 5,859,341; 6,297,426; 5,478,369; 5,824,524; 5,850,014 and 6,265,640; all of which are hereby incorporated by reference.

Also see, U.S. Pat. No. 5,426,041 (discovery relating to a method for the preparation of a seed of a plant comprising crossing a male sterile plant and a second plant which is male fertile), U.S. Pat. No. 6,013,859 (molecular methods of hybrid seed production) and U.S. Pat. No. 6,037,523 (use of male tissue-preferred regulatory region in mediating fertility), all of which are hereby incorporated by reference for this purpose.

5. Genes that Create a Site for Site Specific DNA Integration.

This includes the introduction of FRT sites that may be used in the FLP/FRT system and/or Lox sites that may be used in the Cre/Loxp system. For example, see, Lyznik, et al., (2003) "Site-Specific Recombination for Genetic Engineering in Plants", *Plant Cell Rep* 21:925-932 and WO 99/25821, which are hereby incorporated by reference. Other systems that may be used include the Gin recombinase of phage Mu (Maeser, et al., 1991), the Pin recombinase of *E. coli* (Enomoto, et al., 1983), and the R/RS system of the pSR1 plasmid (Araki, et al., 1992).

6. Genes that Affect Abiotic Stress Resistance (Including but not Limited to Flowering, Ear and Seed Development, Enhancement of Nitrogen Utilization Efficiency, Altered Nitrogen Responsiveness, Drought Resistance or Tolerance, Cold Resistance or Tolerance, and Salt Resistance or Tolerance) and Increased Yield Under Stress.

For example, see, WO 00/73475 where water use efficiency is altered through alteration of malate; U.S. Pat. Nos. 5,892,009, 5,965,705, 5,929,305, 5,891,859, 6,417,428, 6,664,446, 6,706,866, 6,717,034, 6,801,104, WO2000060089, WO2001026459, WO2001035725, WO2001034726, WO2001035727, WO2001036444, WO2001036597, WO2001036598, WO2002015675, WO2002017430, WO2002077185, WO2002079403, WO2003013227, WO2003013228, WO2003014327, WO2004031349, WO2004076638, WO9809521 and WO9938977 describing genes, including CBF genes and transcription factors effective in mitigating the negative effects of freezing, high salinity, and drought on plants, as well as conferring other positive effects on plant phenotype; US Patent Application Publication Number 2004/0148654 and WO01/36596 where abscisic acid is altered in plants resulting in improved plant phenotype such as increased yield and/or increased tolerance to abiotic stress; WO2000/006341, WO04/090143, U.S. patent application Ser. Nos. 10/817,483 and 09/545,334 where cytokinin expression is modified resulting in plants with increased stress tolerance, such as drought tolerance, and/or increased yield. Also see WO0202776, WO03052063, JP2002281975, U.S. Pat. No. 6,084,153, WO0164898, U.S. Pat. No. 6,177,275 and U.S. Pat. No. 6,107,547 (enhancement of nitrogen utilization and altered nitrogen responsiveness). For ethylene alteration, see, US Patent Application Publication Numbers 2004/0128719, 2003/0166197 and WO200032761. For plant transcription factors or transcriptional regulators of abiotic stress, see e.g., US Patent Application Publication Number 2004/0098764 or US Patent Application Publication Number 2004/0078852.

Other genes and transcription factors that affect plant growth and agronomic traits such as yield, flowering, plant growth and/or plant structure, can be introduced or introgressed into plants, see, e.g., WO97/49811 (LHY), WO98/56918 (ESD4), WO97/10339 and U.S. Pat. No. 6,573,430 (TFL), U.S. Pat. No. 6,713,663 (FT), WO96/14414 (CON), WO96/38560, WO01/21822 (VRN1), WO00/44918 (VRN2), WO99/49064 (GI), WO00/46358 (FRI), WO97/29123, U.S. Pat. Nos. 6,794,560, 6,307,126 (GAI), WO99/09174 (D8 and Rht), and WO2004076638 and WO2004031349 (transcription factors).

Seed Cleaning

This discovery is also directed to methods for producing cleaned canola seed by cleaning seed of variety 45H76. "Cleaning a seed" or "seed cleaning" refers to the removal of foreign material from the surface of the seed. Foreign material to be removed from the surface of the seed includes but is not limited to fungi, bacteria, insect material, including insect eggs, larvae, and parts thereof, and any other pests that exist on the surface of the seed. The terms "cleaning a seed" or "seed cleaning" also refer to the removal of any debris or low quality, infested, or infected seeds and seeds of different species that are foreign to the sample. This discovery is also directed to produce subsequent generations of seed from seed of variety 45H76, harvesting the subsequent generation of seed; and planting the subsequent generation of seed.

Seed Treatment

"Treating a seed" or "applying a treatment to a seed" refers to the application of a composition to a seed as a coating or otherwise. The composition may be applied to the seed in a seed treatment at any time from harvesting of the seed to sowing of the seed. The composition may be applied using methods including but not limited to mixing in a container, mechanical application, tumbling, spraying, misting, and immersion. Thus, the composition may be applied as a slurry, a mist, or a soak. The composition to be used as a seed treatment can be a pesticide, fungicide, insecticide, or antimicrobial. For a general discussion of techniques used to apply fungicides to seeds, see "Seed Treatment," 2d ed., (1986), edited by K. A Jeffs (chapter 9), herein incorporated by reference in its entirety.

INDUSTRIAL APPLICABILITY

The seed of the 45H76 variety, the plant produced from such seed, various parts of the 45H76 hybrid canola plant or its progeny, a canola plant produced from the crossing of the 45H76 variety, and the resulting seed, can be utilized in the production of an edible vegetable oil or other food products in accordance with known techniques. The remaining solid meal component derived from seeds can be used as a nutritious livestock feed.

DEPOSIT

Applicant has made a deposit of at least 2500 seeds of canola variety 45H76 with the American Type Culture Collection (ATCC), 10801 University Boulevard, Manassas, Va. 20110-2209 USA, ATCC Deposit No. PTA-122030. The seeds deposited with the ATCC on Feb. 20, 2015 for PTA-122030 were taken from the seed stock maintained by Pioneer Hi-Bred International, Inc., 7250 NW 62$^{nd}$ Avenue, Johnston, Iowa 50131-1000 since prior to the filing date of this application. Access to this deposit will be available during the pendency of the application to the Commissioner of Patents and Trademarks and persons determined by the Commissioner to be entitled thereto upon request. Upon allowance of any claims in the application, the Applicant will make available to the public, pursuant to 37 C.F.R. §1.808, sample(s) of the deposit of at least 2500 seeds of canola variety 45H76 with the American Type Culture Collection (ATCC), 10801 University Boulevard, Manassas, Va. 20110-2209. This deposit of seed of canola variety 45H76 will be maintained in the ATCC depository, which is a public depository, for a period of 30 years, or 5 years after the most recent request, or for the enforceable life of the patent, whichever is longer, and will be replaced if it becomes nonviable during that period. Additionally, Applicant has satisfied all the requirements of 37 C.F.R. §§1.801-1.809, including providing an indication of the viability of the sample upon deposit. Applicant has no authority to waive any restrictions imposed by law on the transfer of biological material or its transportation in commerce. Applicant(s) do not waive any infringement of their rights granted under this patent or rights applicable to canola hybrid 45H76 under the Plant Variety Protection Act (7 USC 2321 et seq.).

| Varietal Characteristics (See also Tables 1 through 4) | |
|---|---|
| Seed yield | 1.3% lower than the mean of the WCC/RRC checks. |
| Disease reaction | Classified as Resistant (R) to blackleg (Leptospaera maculans) according to WCC/RRC guidelines. Classified as resistant (R) to Fusarium wilt according to trials. |
| Plant height | Approximately 1.5 cm taller than the mean of the WCC/RRC checks. |
| Maturity | Approximately 1 day later maturing than the WCC/RRC checks. |
| Lodging | Slightly poorer lodging than the WCC/RRC checks. |
| Herbicide tolerance | Tolerant to imidazolinone herbicides. Field testing confirms that 45H76 tolerates the recommended rate of Solo WDG (Imazamox) (35 g ai/ha) without showing plant injury or any significant negative effect on yield, agronomic, and quality traits. |
| Variants | Exhibits less than 1500/10,000 (<15%) sterile plants. |
| | Seed Characteristics |
| Seed color | Dark brown |
| Grain size | 1000 seed weight is 0.3 g greater than the mean of the WCC/RRC checks. |
| Seed oil content | Approximately equal to the mean of the WCC/RRC checks. |
| Seed protein content | 0.5% greater than the mean of the WCC/RRC checks. |
| | Erucic acid Less than 0.5% (maximum allowable limit). |
| Total saturates | 0.1% lower than the mean of the WCC/RRC checks. |
| Total glucosinolates | Canola quality ? lower than the WCC/RRC checks. |
| Chlorophyll | 0.5 ppm greater than the mean of the WCC/RRC checks. |

TABLE 1

Variety Descriptions based on Morphological, Agronomic and Quality Traits

| | | 45H76 | | 46H75 (Check Variety) | |
|---|---|---|---|---|---|
| Trait Code | Trait | Mean | Description | Mean | Description |
| 1.2 | Seasonal Type | | Spring | | |
| 2.1 | Cotyledon width<br>3 = narrow<br>5 = medium<br>7 = wide | 5 | Medium | 4 | Narrow to Medium |
| 2.2 | Seedling growth habit (leaf rosette)<br>1 = weak rosette<br>9 = strong rosette | 5 | | 5 | |
| 2.3 | Stem anthocyanin intensity<br>1 = absent or very weak<br>3 = weak<br>5 = medium<br>7 = strong<br>9 = very strong | 1 | Absent or very weak | 2 | Absent or very weak to Weak |
| 2.4 | Leaf type<br>1 = petiolate<br>9 = lyrate | 1 | Petiolate | 1 | Petiolate |
| 2.5 | Leaf shape<br>3 = narrow elliptic<br>7 = orbicular | 3 | Narrow elliptic | 3 | Narrow elliptic |
| 2.6 | Leaf length<br>3 = short<br>5 = medium<br>7 = long | 6 | Medium/Long | 5 | Medium |
| 2.7 | Leaf width<br>3 = narrow<br>5 = medium<br>7 = wide | 5 | Medium | 5 | Medium |

TABLE 1-continued

Variety Descriptions based on Morphological, Agronomic and Quality Traits

| Trait Code | Trait | 45H76 Mean | 45H76 Description | 46H75 (Check Variety) Mean | 46H75 (Check Variety) Description |
|---|---|---|---|---|---|
| 2.8 | Leaf color<br>1 = light green<br>2 = medium green<br>3 = dark green<br>4 = blue-green | 2 | Medium green | 2 | Medium green |
| 2.12 | Leaf lobe development<br>1 = absent or very weak<br>3 = weak<br>5 = medium<br>7 = strong<br>9 = very strong | 4 | Weak to Medium | 4 | Weak to Medium |
| 2.13 | Number of leaf lobes | 3 | | 3 | |
| 2.15 | Petiole length<br>3 = short<br>5 = medium<br>7 = long | 5 | Medium | 5 | Medium |
| 2.16 | Leaf margin shape<br>1 = undulating<br>2 = rounded<br>3 = sharp | 3 | Sharp | 3 | Sharp |
| 2.17 | Leaf margin indentation<br>1 = absent or very weak (very shallow)<br>3 = weak (shallow)<br>5 = medium<br>7 = strong (deep)<br>9 = very strong (very deep) | 4 | Weak (shallow) to Medium | 4 | Weak (shallow) to Medium |
| 2.18 | Leaf attachment to stem<br>1 = complete clasping<br>2 = partial clasping<br>3 = non-clasping | 2 | Partial clasping | 2 | Partial clasping |
| 3.1 | Flower date 50% | 49.3 | | | |
| 3.2 | Plant height at maturity<br>3 = short<br>5 = medium<br>7 = tall | 6 | Medium/Tall | | |
| 3.4 | Flower bud location<br>1 = buds above most recently opened flowers<br>9 = buds below most recently opened flowers | 1 | Buds above most recently opened flowers | 1 | Buds above most recently opened flowers |
| 3.5 | Petal color<br>1 = white<br>2 = light yellow<br>3 = medium yellow<br>4 = dark yellow<br>5 = orange<br>6 = other | 3 | Medium yellow | 3 | Medium yellow |
| 3.6 | Petal length<br>3 = short<br>5 = medium<br>7 = long | 5 | Medium | 5 | Medium |
| 3.7 | Petal width<br>3 = narrow<br>5 = medium<br>7 = wide | 5 | Medium | 5 | Medium |
| 3.8 | Petal spacing<br>1 = open<br>3 = not touching<br>5 = touching<br>7 = slight overlap<br>9 = strongly overlap | 4 | Not touching to Touching | 2 | Open to Not touching |
| 3.11 | Anther fertility<br>1 = sterile<br>9 = all anthers shedding pollen | 9 | All anthers shedding pollen | 9 | All anthers shedding pollen |
| 3.12 | Pod (silique) length<br>1 = short (<7 cm)<br>5 = medium (7-10 cm)<br>9 = long (>10 cm) | 5 | Medium | 4 | |
| 3.13 | Pod (silique) width<br>3 = narrow (3 mm)<br>5 = medium (4 mm)<br>7 = wide (5 mm) | 5 | Medium (4 mm) | 6 | Medium (4 mm) to Wide (5 mm) |
| 3.14 | Pod (silique) attitude<br>1 = erect<br>3 = semi-erect<br>5 = horizontal<br>7 = slightly drooping<br>9 = drooping | 3 | Semi-erect | 3 | Semi-erect |
| 3.15 | Pod (silique) beak length<br>3 = short<br>5 = medium<br>7 = long | 5 | Medium | 5 | Medium |
| 3.16 | Pedicel length<br>3 = short<br>5 = medium<br>7 = long | 6 | Medium to Long | 5 | Medium |
| 3.17 | Maturity (days from planting) | 99.5 | | | |
| 4.1 | Seed coat color<br>1 = black<br>2 = brown<br>3 = tan<br>4 = yellow<br>5 = mixed<br>6 = other | 1.5 | Black to brown | 1.5 | Black to brown |
| 4.3 | Seed weight/Thousand seed weight (5-6% moisture content): grams per 1,000 seeds | 3.7 | | | |
| 5.1 | Shatter resistance<br>1 = Not tested<br>3 = Poor<br>5 = Fair<br>7 = Good<br>9 = Does not shatter | 1 | Not tested | 1 | Not tested |
| 5.2 | Lodging resistance<br>1 = not tested<br>3 = poor<br>5 = fair<br>7 = good<br>9 = excellent | 5.9 | | | |
| 6.3 | Blackleg resistance<br>0 = not tested<br>1 = resistant<br>3 = moderately resistant<br>5 = moderately | 1 | Resistant | | |

TABLE 1-continued

Variety Descriptions based on Morphological, Agronomic and Quality Traits

| Trait Code | Trait | 45H76 Mean | 45H76 Description | 46H75 (Check Variety) Mean | 46H75 (Check Variety) Description |
|---|---|---|---|---|---|
| | susceptible | | | | |
| | 7 = susceptible | | | | |
| | 9 = highly susceptible | | | | |
| 6.7 | Fusarium wilt resistance | 1 | Resistant | | |
| | 0 = not tested | | | | |
| | 1 = resistant | | | | |
| | 3 = moderately resistant | | | | |
| | 5 = moderately susceptible | | | | |
| | 7 = susceptible | | | | |
| | 9 = highly susceptible | | | | |
| 8.1 | Oil content percentage | 49.12 | | | |
| 8.5 | Protein percentage (whole dry seed) | 44.89 | | | |
| 8.7 | Glucosinolates (μmoles total glucs/g whole seed) | 2 | Low (10-15 μmol per gram) | | |
| | 1 = very low (<10) | | | | |
| | 2 = low (10-15) | | | | |
| | 3 = medium (15-20) | | | | |
| | 4 = high (>20) | | | | |
| 8.8 | Chlorophyll content (mg/kg seed) | 2 | Medium (8-15 ppm) | | |
| | 1 = low (<8 ppm) | | | | |
| | 2 = medium (8-15 ppm) | | | | |
| | 3 = high (>15 ppm) | | | | |

EXAMPLE 1

Herbicide Resistance

Appropriate field tests have shown that 45H76 tolerates the recommended rate of Solo WDG (Imazamox) (35 g ai/ha) without showing plant injury or any significant negative effect on yield, agronomic, and quality traits.

TABLE 2

Effect of herbicide application on agronomic and quality traits of 45H76 in herbicide tolerance trials in 2011 and 2012

| Variety | Treatment | Yield q/ha | Yield (% WF) | HIN 10 | HIN 21 | Days to Flower | Height (cm) | Days to Maturity | % Oil | % Protein | Oil + Protein | Gluc's @ 8.5% | Chlorophyll |
|---|---|---|---|---|---|---|---|---|---|---|---|---|---|
| \multicolumn{14}{c}{2011 Ellerslie, AB 2ESH} | | | | | | | | | | | | | |
| 45H76 | 2X | 35.7 | 92.2 | 1.0 | 0.0 | 52.0 | 126.0 | 115.0 | 48.9 | 44.5 | 93.4 | 14.0 | 8.0 |
| 45H76 | WF | 38.7 | | 0.0 | 0.0 | 52.0 | 127.0 | 115.0 | 48.4 | 46.1 | 94.5 | 14.0 | 6.0 |
| CV % | | 9.30 | | 79.6 | 105.7 | 1.0 | 5.3 | 0.6 | 2.2 | 3.1 | 0.7 | 8.3 | 18.4 |
| LSD (0.05) | | 5.10 | | 2.0 | 0.0 | 1.0 | 10.0 | 1.0 | 2.2 | 3.0 | 1.3 | 2.0 | 4.0 |
| SE | | 1.77 | | 0.71 | 0.00 | 0.00 | 3.54 | 0.00 | 0.78 | 1.06 | 0.50 | 0.71 | 1.41 |
| \multicolumn{14}{c}{2011 Saskatoon, SK 2SSH} | | | | | | | | | | | | | |
| 45H76 | 2X | 20.5 | 77.9 | 1.0 | 0.0 | 50.0 | 101.0 | 96.0 | 50.9 | 41.6 | 92.5 | 10.0 | 14.0 |
| 45H76 | WF | 26.3 | | 0.0 | 0.0 | 50.0 | 100.0 | 96.0 | 49.3 | 44.8 | 94.1 | 12.0 | 14.0 |
| CV % | | 14.3 | | 58.6 | 271.6 | 1.3 | 8.6 | 0.5 | 1.6 | 2.9 | 0.8 | 10.4 | 21.7 |
| LSD (0.05) | | 5.3 | | 1.0 | 3.0 | 1.0 | 13.0 | 1.0 | 1.2 | 1.8 | 1.3 | 1.0 | 7.0 |
| SE | | 1.84 | | 0.71 | 0.71 | 0.71 | 4.24 | 0.00 | 0.42 | 0.64 | 0.42 | 0.71 | 2.12 |
| \multicolumn{14}{c}{2011 Treherne, MB 3TRY} | | | | | | | | | | | | | |
| 45H76 | 2X | 24.4 | 102.1 | 0.0 | 0.0 | | 112.0 | 91.0 | 46.9 | 47.4 | 94.4 | 12.0 | 7.0 |
| 45H76 | WF | 23.9 | | 0.0 | 0.0 | | 109.0 | 92.0 | 48.9 | 45.6 | 94.5 | 12.0 | 5.0 |
| CV % | | 14.3 | | 114.5 | 204.7 | | 6.5 | 2.0 | 2.4 | 2.7 | 0.5 | 10.1 | 31.2 |
| LSD (0.05) | | 4.7 | | 2.0 | 0.0 | | 11.0 | 3.0 | 2.4 | 2.6 | 1.0 | 2.0 | 7.0 |
| SE | | 1.70 | | 0.71 | 0.0 | | 4.24 | 0.71 | 0.8 | 0.92 | 0.35 | 0.71 | 2.12 |
| \multicolumn{14}{c}{2011 Carman, MB 3CRY} | | | | | | | | | | | | | |
| 45H76 | 2X | 31.4 | 102.3 | 0.0 | 0.0 | 47.0 | 115.0 | 90.0 | 47.9 | 45.8 | 93.7 | 13.0 | 11.0 |
| 45H76 | WF | 30.7 | | 0.0 | 0.0 | 45.0 | 130.0 | 89.0 | 48.1 | 46.2 | 94.3 | 13.0 | 13.0 |
| CV % | | 10.7 | | 85.1 | 169.5 | 1.4 | 6.4 | 1.8 | 1.6 | 1.6 | 0.5 | 7.9 | 22.5 |
| LSD (0.05) | | 4.4 | | 1.0 | 0.0 | 1.0 | 10.0 | 2.0 | 1.8 | 1.9 | 0.9 | 2.0 | 6.0 |
| SE | | 1.56 | | 0.71 | 0.00 | 0.00 | 3.54 | 0.71 | 0.64 | 0.71 | 0.35 | 0.71 | 2.12 |
| \multicolumn{14}{c}{2011 Average} | | | | | | | | | | | | | |
| 45H76 | 2X | 28.0 | 94.0 | 0.0 | 0.0 | 50.0 | 114.0 | 98.0 | 48.8 | 44.6 | 93.4 | 12.0 | 9.0 |
| 45H76 | WF | 29.8 | | 0.0 | 0.0 | 49.0 | 117.0 | 98.0 | 48.4 | 46.0 | 94.4 | 13.0 | 9.0 |
| CV % | | 12.1 | | 105.4 | 356.7 | 1.4 | 7.1 | 1.5 | 2.2 | 2.8 | 0.8 | 12.3 | 31.8 |
| LSD (0.05) | | 2.5 | | 1.0 | 1.0 | 1.0 | 6.0 | 1.0 | 1.0 | 1.3 | 0.7 | 1.0 | 4.0 |
| SE | | 0.92 | | 0.0 | 0.0 | 0.0 | 2.1 | 0.7 | 0.4 | 0.4 | 0.3 | 0.7 | 1.4 |
| \multicolumn{14}{c}{2012 Vegreville, AB 2VGH} | | | | | | | | | | | | | |

TABLE 2-continued

Effect of herbicide application on agronomic and quality traits of 45H76 in herbicide tolerance trials in 2011 and 2012

| Variety | Treatment | Yield q/ha | Yield (% WF) | HIN 10 | HIN 21 | Days to Flower | Height (cm) | Days to Maturity | % Oil | % Protein | Oil + Protein | Gluc's @ 8.5% | Chlorophyll |
|---|---|---|---|---|---|---|---|---|---|---|---|---|---|
| 45H76 | 2X | 13.6 | 101.5 | 1.0 | 0.0 | 53.0 | 95.0 | 100.0 | 46.3 | 47.5 | 93.8 | 20.7 | 1.8 |
| 45H76 | WF | 13.4 | | 0.0 | 0.0 | 53.0 | 100.0 | 100.0 | 45.7 | 48.8 | 94.5 | 21.3 | 3.2 |
| CV % | | 10.30 | | 154.0 | 339.4 | 1.8 | 4.1 | 1.2 | 1.9 | 1.9 | 0.6 | 9.1 | 39.5 |
| LSD (0.05) | | 2.60 | | 2.0 | 1.0 | 1.0 | 6.0 | 2.0 | 3.0 | 2.9 | 1.2 | 3.7 | 11.5 |
| SE | | 0.92 | | 0.71 | 0.00 | 0.71 | 2.12 | 0.71 | 1.06 | 1.06 | 0.42 | 1.34 | 4.10 |
| | | | | | | 2012 Saskatoon, SK 2SSH | | | | | | | |
| 45H76 | 2X | 11.5 | 113.9 | 1.0 | 0.0 | | 104.0 | 102.0 | 47.5 | 45.5 | 93.0 | 17.1 | 13.2 |
| 45H76 | WF | 10.1 | | 0.0 | 0.0 | | 106.0 | 100.0 | 46.7 | 45.5 | 92.2 | 17.5 | 13.0 |
| CV % | | 15.3 | | 425.0 | 0.0 | | 7.9 | 0.7 | 2.4 | 1.6 | 0.9 | 9.1 | 23.0 |
| LSD (0.05) | | 2.5 | | 1.0 | | | 13.0 | 1.0 | 2.6 | 1.8 | 1.7 | 3.0 | 14.7 |
| SE | | 0.85 | | 0.00 | | | 4.24 | 0.71 | 0.92 | 0.64 | 0.57 | 1.06 | 5.23 |
| | | | | | | 2012 Average | | | | | | | |
| 45H76 | 2X | 12.6 | 106.8 | 1.0 | 0.0 | 53.0 | 99.0 | 101.0 | 46.9 | 46.5 | 93.4 | 18.9 | 7.5 |
| 45H76 | WF | 11.8 | | 0.0 | 0.0 | 53.0 | 103.0 | 100.0 | 46.2 | 47.1 | 93.3 | 19.4 | 8.1 |
| CV % | | 14.6 | | 250.8 | 646.3 | 1.8 | 6.6 | 1.2 | 2.5 | 2.3 | 0.9 | 12.7 | 31.1 |
| LSD (0.05) | | 2.1 | | 1.0 | 0.0 | 1.0 | 7.0 | 1.0 | 2.2 | 2.1 | 1.3 | 2.9 | 10.9 |
| SE | | 0.78 | | 0.71 | 0.00 | 0.71 | 2.83 | 0.71 | 0.78 | 0.71 | 0.42 | 1.06 | 3.89 |
| | | | | | | 2 Year Average | | | | | | | |
| 45H76 | 2X | 22.9 | 95.8 | 0.7 | 0.0 | 50.5 | 108.8 | 99.0 | 48.1 | 45.4 | 93.5 | 14.5 | 9.2 |
| 45H76 | WF | 23.9 | | 0.0 | 0.0 | 50.0 | 112.0 | 98.7 | 47.9 | 46.2 | 94.0 | 15.0 | 9.0 |
| CV % | | 12.4 | | 152.8 | 218.2 | 1.4 | 6.5 | 1.1 | 2.0 | 2.3 | 0.7 | 9.2 | 26.1 |
| LSD (0.05) | | 4.1 | | 1.5 | 1.2 | 1.1 | 10.5 | 1.8 | 2.1 | 2.5 | 1.4 | 2.3 | 9.2 |
| SE | | 1.49 | | 0.55 | 0.44 | 0.38 | 3.80 | 0.64 | 0.76 | 0.89 | 0.52 | 0.84 | 3.32 |

EXAMPLE 2

Miscellaneous Disease Resistance

Blackleg

Blackleg tolerance was measured following the standard procedure described in the Procedures of the Western Canada Canola/Rapeseed Recommending Committee (WCC/RRC) Incorporated for the Evaluation and Recommendation for Registration of Canola/Rapeseed Candidate Cultivars in Western Canada. Blackleg was rated on a scale of 0 to 5: a plant with zero rating is completely immune to disease while a plant with "5" rating is dead due to blackleg infection.

Canola variety "Westar" was included as an entry/control in each blackleg trial. Tests are considered valid when the mean rating for Westar is greater than or equal to 2.6 and less than or equal to 4.5. (In years when there is poor disease development in Western Canada the WCC/RRC may accept the use of data from trials with a rating for Westar exceeding 2.0.)

The ratings are converted to a percentage severity index for each line, and the following scale is used to describe the level of resistance:

| Classification | Rating (% of Westar) |
|---|---|
| R (Resistant) | <30 |
| MR (Moderately Resistant) | 30-49 |
| MS (Moderately Susceptible) | 50-69 |
| S (Susceptible) | 70-89 |
| HS (Highly Susceptible) | 90-100 |

TABLE 3

Summary of Blackleg Ratings for 45H76

2012

| | Alvena | Boissevain | Carman | North Battleford | Plum Coulee | Roland | Saskatoon | Vegreville | Average | % Westar | Class |
|---|---|---|---|---|---|---|---|---|---|---|---|
| 45H76 | 1.3 | 0.5 | 0.4 | 0.4 | 1.1 | 1.3 | 1.0 | 1.7 | 1.0 | 26.5 | R |
| Westar | 4.3 | 3.2 | 3.0 | 3.5 | 3.6 | 3.8 | 3.9 | 3.5 | 3.6 | | |

EXAMPLE 3

Summary of Performance of 45H76 in Two Years of Co-Op Testing

Two years (2012 and 2013) of trials were conducted. WCC/RRC guidelines were followed for conducting trials. Each trial had four replicates and had a plot size of 1.5 m×6 m. Yield and agronomic traits were recorded and seed samples were collected from two of the four replicates at selected sites and were analyzed for quality traits such as oil and protein percent at 8.5% moisture, total whole seed glucosinolates at 8.5%, chlorophyll, total saturated fatty acid, 1000 seed weight etc. WCC/RRC guidelines were followed for analyzing quality parameters.

TABLE 4

Summary of Performance of 45H76 in two years of Co-op Testing

| Variety | Yield (q/ha) | Yield % WCC/RRC Checks | Days to Maturity | Days to Flower | Early Vigor (1 = poor, 9 = best) | Lodging Score (1 = poor, 9 = best) | Plant Height (cm) | Oil % @ zero moisture | Protein % (oil free) | Total Glucs (umol/g) | Total Saturated Fat (%) | Chlorophyll (ppm) | Green Seed % | 1000 Seed Weight (g) |
|---|---|---|---|---|---|---|---|---|---|---|---|---|---|---|
| 2011 | | | | | | | | | | | | | | |
| 45H76 | 26.1 | 96 | 104 | 51.6 | 6.6 | 6.4 | 118.8 | 50.2 | 44.0 | 11.7 | 6.4 | 12.0 | 1.0 | 3.7 |
| 5440 | 27.5 | 102 | 103 | 51.0 | 6.1 | 7.2 | 118.0 | 49.2 | 43.4 | 11.5 | 6.4 | 13.0 | 0.7 | 3.4 |
| 45H29 | 26.6 | 98 | 103 | 50.2 | 6.0 | 5.8 | 118.7 | 50.9 | 44.1 | 12.6 | 6.6 | 10.0 | 0.9 | 3.3 |
| Loc | 19 | 19 | 19 | 10 | 14 | 4 | 9 | 10 | 18 | 18 | 18 | 18 | 17 | 17 |
| CHK-AVG | 27.0 | 100 | 103 | 50.6 | 6.1 | 6.5 | 118.4 | 50.1 | 43.7 | 12.1 | 6.5 | 11.5 | 0.8 | 3.4 |
| DIFF | −0.9 | −3.5 | 0.8 | 1.0 | 0.6 | −0.1 | 0.5 | 0.1 | 0.2 | −0.4 | −0.1 | 0.5 | 0.3 | 0.3 |
| 2012 | | | | | | | | | | | | | | |
| 45H76 | 25.3 | 94 | 95 | 47.4 | | 5.8 | 114.3 | 45.6 | 50.5 | 11.1 | 6.2 | | | |
| 5440 | 27.4 | 102 | 94 | 46.5 | | 6.5 | 112.6 | 45.9 | 47.6 | 10.2 | 6.4 | | | |
| 45H29 | 26.5 | 98 | 93 | 46.3 | | 5.5 | 112.3 | 46.6 | 49.0 | 14.8 | 6.5 | | | |
| Loc | 17 | 17 | 16 | 12 | | 13 | 16 | 3 | 3 | 3 | 3 | | | |
| CHK-AVG | 26.9 | 100 | 94 | 46.4 | | 6.0 | 112.5 | 46.2 | 48.3 | 12.5 | 6.4 | | | |
| DIFF | −1.6 | −6.0 | 1.2 | 1.0 | | −0.2 | 1.9 | −0.6 | 2.3 | −1.4 | −0.2 | | | |
| 2 Year Average | | | | | | | | | | | | | | |
| 45H76 | 25.7 | 95 | 100 | 49.3 | 6.6 | 5.9 | 115.9 | 49.1 | 44.9 | 11.6 | 6.4 | 12.0 | 1.0 | 3.7 |
| 5440 | 27.4 | 102 | 99 | 48.5 | 6.1 | 6.7 | 114.5 | 48.5 | 44.0 | 11.3 | 6.4 | 13.0 | 0.7 | 3.4 |
| 45H29 | 26.6 | 98 | 98 | 48.1 | 6.0 | 5.6 | 114.6 | 49.9 | 44.8 | 12.9 | 6.6 | 10.0 | 0.9 | 3.3 |
| Loc | 36 | 36 | 35 | 22 | 14 | 17 | 25 | 13 | 21 | 21 | 21 | 18 | 17 | 17 |
| CHK-AVG | 27.0 | 100 | 99 | 48.3 | 6.1 | 6.1 | 114.6 | 49.2 | 44.4 | 12.1 | 6.5 | 11.5 | 0.8 | 3.4 |
| DIFF | −1.3 | −4.7 | 1.0 | 1.0 | 0.6 | −0.2 | 1.3 | 0.0 | 0.5 | −0.5 | −0.1 | 0.5 | 0.3 | 0.3 |

The foregoing discovery has been described in detail by way of illustration and example for purposes of exemplification. However, it will be apparent that changes and modifications such as single gene modifications and mutations, somaclonal variants, variant individuals selected from populations of the plants of the instant variety, and the like, are considered to be within the scope of the present discovery. All references disclosed herein whether to journal, patents, published applications and the like are hereby incorporated in their entirety by reference.

What is claimed is:

1. A canola variety 45H76, representative seed of the variety having been deposited under ATCC Accession Number PTA-122030.

2. A seed of the canola variety of claim 1.

3. The seed of claim 2, further comprising a seed treatment.

4. The seed of claim 3, wherein the treatment comprises a fungicide or insecticide.

5. A method comprising cleaning the seed of claim 2.

6. A method of producing a canola seed, the method comprising planting the seed of claim 2 to produce a subsequent generation of seed; harvesting the subsequent generation of seed; and planting the subsequent generation of seed.

7. The seed of claim 2, further comprising a trait introduced by backcrossing or genetic transformation.

8. The seed of claim 7, wherein the trait is selected from the group consisting of male sterility, a site for site-specific recombination, abiotic stress tolerance, altered phosphate, altered antioxidants, altered fatty acids, altered essential amino acids, altered carbohydrates, herbicide resistance, insect resistance and disease resistance.

9. The seed of claim 7, further comprising a seed treatment.

10. The seed of claim 9, wherein the treatment comprises a fungicide or insecticide.

11. A method comprising cleaning the seed of claim 7.

12. A plant or plant part of the canola variety of claim 1.

13. A method of producing a second canola plant, the method comprising applying plant breeding techniques to the plant or plant part of claim 12, thereby producing the second canola plant.

14. A method for producing a canola plant derived from canola variety 45H76, the method comprising:
   (a) crossing the plant of claim 12 with itself or a second plant to produce progeny seed;
   (b) growing the progeny seed to produce a progeny plant and crossing the progeny plant with itself or a different plant to produce further progeny seed; and
   (c) repeating step (b) for at least one additional generation to produce a canola plant derived from the variety 45H76.

15. A method for producing a second canola plant or plant part, the method comprising doubling haploid seed generated from the plant of claim 12, thereby producing the second canola plant or plant part.

16. The plant or plant part of claim 12, further comprising a trait introduced by backcrossing or genetic transformation.

17. The plant or plant part of claim 16, wherein the trait is selected from the group consisting of male sterility, a site for site-specific recombination, abiotic stress tolerance, altered phosphate, altered antioxidants, altered fatty acids, altered essential amino acids, altered carbohydrates, herbicide resistance, insect resistance and disease resistance.

18. A method for producing a second canola plant or plant part, the method comprising applying plant breeding techniques to the plant or plant part of claim 16, thereby producing the second canola plant.

19. A method for producing a canola plant derived from canola variety 45H76, the method comprising:
   (a) crossing the plant of claim 16 with itself or a second plant to produce progeny seed;
   (b) growing the progeny seed to produce a progeny plant and crossing the progeny plant with itself or a different plant to produce further progeny seed; and
   (c) repeating step (b) for at least one additional generation to produce a canola plant derived from the variety 45H76 and further comprising the trait.

20. A method for producing a second canola plant or plant part, the method comprising doubling haploid seed generated from the plant of claim 16, thereby producing the second canola plant or plant part.

\* \* \* \* \*